US010584352B2

(12) United States Patent
Duchateau et al.

(10) Patent No.: US 10,584,352 B2
(45) Date of Patent: Mar. 10, 2020

(54) METHODS FOR ENGINEERING T CELLS FOR IMMUNOTHERAPY BY USING RNA-GUIDED CAS NUCLEASE SYSTEM

(71) Applicant: Cellectis, Paris (FR)

(72) Inventors: Philippe Duchateau, Draveil (FR); André Choulika, Paris (FR); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 0 days.

(21) Appl. No.: 15/891,496

(22) Filed: Feb. 8, 2018

(65) Prior Publication Data

US 2018/0237798 A1 Aug. 23, 2018

Related U.S. Application Data

(63) Continuation of application No. 14/892,934, filed as application No. PCT/EP2014/056534 on Apr. 1, 2014, now Pat. No. 9,890,393.

(60) Provisional application No. 61/888,259, filed on Oct. 8, 2013, provisional application No. 61/907,858, filed on Nov. 22, 2013, provisional application No. 61/907,874, filed on Nov. 22, 2013.

(30) Foreign Application Priority Data

May 29, 2013 (DK) .................................. 2013 70297
Dec. 13, 2013 (DK) .................................. 2013 70771

(51) Int. Cl.
| | |
|---|---|
| *A61K 35/17* | (2015.01) |
| *C12N 15/85* | (2006.01) |
| *C12N 5/0783* | (2010.01) |
| *C12N 9/22* | (2006.01) |
| *C12N 15/90* | (2006.01) |
| *C12N 15/113* | (2010.01) |

(52) U.S. Cl.
CPC .............. *C12N 15/85* (2013.01); *A61K 35/17* (2013.01); *C12N 5/0636* (2013.01); *C12N 5/0637* (2013.01); *C12N 5/0638* (2013.01); *C12N 9/22* (2013.01); *C12N 15/90* (2013.01); *C12N 15/1138* (2013.01); *C12N 2310/20* (2017.05); *C12N 2510/00* (2013.01); *C12Y 301/00* (2013.01)

(58) Field of Classification Search
CPC ...................................................... A61K 35/17
See application file for complete search history.

(56) References Cited

U.S. PATENT DOCUMENTS 8,486,911 B2 * 7/2013 Okada .................. C12N 5/0636
514/44 A

FOREIGN PATENT DOCUMENTS

| | | |
|---|---|---|
| WO | 2013/074916 A1 | 5/2013 |
| WO | 2013/176915 A1 | 11/2013 |

OTHER PUBLICATIONS

Torikai et al. (e-Pub Apr. 24, 2012, Blood, vol. 119(24), pp. 5697-5705) (Year: 2012).*
Mali et al. (e-Pub Jan. 3, 2013, Science, vol. 339(6121), pp. 823-826) (Year: 2013).*
H. Torikai et al: "A foundation for universal T-cell based immunotherapy: T cells engineered to express a CD19-specific chimeric-antigen-receptor and eliminate expression of endogenous TCR", Blood, vol. 119, No. 24, Jun. 14, 2012 (Jun. 14, 2012), pp. 5697-5705.
Laurent Poirot et al: "T-Cell Engineering for Adoptive Immunotherapy Using TAL-Effector Nucleases (TALENTM)", Molecular Therapy, Nature Publishing Group, GB, vol. 21, No. Suppl.1, May 17, 2013 (May 17, 2013), p. S154.
Wei Chuanxian et al: "TALEN or Cas9—Rapid, Efficient and Specific Choices for Genome Modificat", Journal of Genetics and Genomics, Elsevier BV, NL, vol. 40, No. 6, Apr. 12, 2013 (Apr. 12, 2013), pp. 281-289.
P. Mali et al: "RNA-Guided Human Genome Engineering via Cas9", Science, vol. 339, No. 6121, Jan. 3, 2013 (Jan. 3, 2013), pp. 823-826.
Gaj Thomas et al: "ZFN, TALEN, and CRISPR/Cas-based methods for genome engineering", Trends in Biotechnology, Elsevier Publications, Cambridge, GB, vol. 31, No. 7, Apr. 4, 2013 (Apr. 4, 2013), pp. 397-405.
Seung Woo Cho et al: "Targeted genome engineering in human cells with the Cas9 RNA-guided endonuclease", Nature Biotechnology, Nature Publishing Group, New York, NY, US, vol. 31, No. 3, Jan. 29, 2013 (Jan. 29, 2013), pp. 230-232.
Kochenderfer J N et al: "Treating B-cell cancer with T cells expressing anti-CD19 chimeric antigen receptors", Nature Reviews Clinical Oncology, Nature, NY, US, vol. 10, No. 5, Apr. 2, 2013 (Apr. 2, 2013), pp. 267-276.

(Continued)

*Primary Examiner* — Thaian N. Ton
*Assistant Examiner* — David A. Montanari
(74) *Attorney, Agent, or Firm* — Arrigo, Lee, Guttman & Mouta-Bellum LLP

(57) ABSTRACT

The present invention relates to methods of developing genetically engineered, preferably non-alloreactive T-cells for immunotherapy. This method involves the use of RNA-guided endonucleases, in particular Cas9/CRISPR system, to specifically target a selection of key genes in T-cells. The engineered T-cells are also intended to express chimeric antigen receptors (CAR) to redirect their immune activity towards malignant or infected cells. The invention opens the way to standard and affordable adoptive immunotherapy strategies using T-Cells for treating cancer and viral infections.

20 Claims, 5 Drawing Sheets

Specification includes a Sequence Listing.

(56) References Cited

OTHER PUBLICATIONS

B. Jena et al: "Redirecting T-cell specificity by introducing a tumor-specific chimeric antigen receptor", Blood, vol. 116, No. 7, Aug. 19, 2010 (Aug. 19, 2010), pp. 1035-1044.
Hirotaka Ebina et al: "Harnessing the CRISPR/Cas9 system to disrupt latent HIV-1 provirus", Scientific Reports, vol. 3, Aug. 26, 2013.
N. Manjunath et al: "Newer Gene Editing Technologies toward HIV Gene Therapy", Viruses, vol. 5, No. 11, Nov. 14, 2013 (Nov. 14, 2013), pp. 2748-2766.
Angharad Lloyd et al: "Beyond the Antigen Receptor: Editing the Genome of T-Cells for Cancer Adoptive Cellular Therapies", Frontiers in Immunology, vol. 4, Aug. 5, 2013.
Prashant Mali et al: "Cas9 as a versatile tool for engineering biology", Nature Methods, Nature Publishing Group, GB, vol. 10, No. 10, Sep. 27, 2013 (Sep. 27, 2013), pp. 957-963.

\* cited by examiner

METHODS FOR ENGINEERING T CELLS FOR IMMUNOTHERAPY BY USING RNA-GUIDED CAS NUCLEASE SYSTEM

SEQUENCE LISTING

The instant application contains a Sequence Listing which has been submitted electronically in ASCII format and is hereby incorporated by reference in its entirety. Said ASCII copy, created on Feb. 15, 2016, is named P81400433US00_SL.txt and is 47,236 bytes in size.

FIELD OF THE INVENTION

The present invention relates to methods of developing genetically engineered, preferably non-alloreactive T-cells for immunotherapy. This method involves the use of RNA-guided endonucleases, in particular Cas9/CRISPR system, to specifically target a selection of key genetic loci in T-cells. The engineered T-cells are also intended to express chimeric antigen receptors (CAR) to redirect their immune activity towards malignant or infected cells. The invention opens the way to standard and affordable adoptive immunotherapy strategies using T-Cells for treating cancer, viral infections and auto-immune diseases.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous T-cell receptors (TCR) specificities recognize the host tissue as foreign, resulting in graft versus host disease (GvHD), which can lead to serious tissue damage and death.

In order to effectively obtain allogeneic cells, the inventors previously disclosed a method to genetically engineer T-Cells, in which different effector genes, in particular those encoding T-cell receptors, were inactivated by using specific TAL-nucleases, better known under the trade mark TALENT™ (Cellectis, 8, rue de la Croix Jarry, 75013 PARIS). This method has proven to be highly efficiency in primary cells using RNA transfection as part of a platform allowing the mass production of allogeneic T-cells (WO 2013/176915).

Recently, a new genome engineering tool has been developed based on the components of the type II prokaryotic CRISPR (Clustered Regularly Interspaced Short palindromic Repeats) adaptive immune system of the bacteria *S. pyogenes*. This multi-component system referred to as RNA-guided Cas nuclease system (Gasiunas, Barrangou et al. 2012; Jinek, Chylinski et al. 2012) or more simply as CRISPR, involves a Cas endonuclease coupled with a guide RNA molecules that have the ability to drive said nuclease to some specific genome sequences. Where the RNA guide hybridizes the genome sequence, the endonuclease has the ability to cleave the DNA. The CRISPR/CRISPR-associated (Cas) system involves 1) retention of foreign genetic material, called "spacers", in clustered arrays in the host genome, 2) expression of short guiding RNAs (crRNAs) from the spacers, 3) binding of the crRNAs to specific portions of the foreign DNA called protospacers and 4) degradation of protospacers by CRISPR-associated nucleases (Cas). The specificity of binding to the foreign DNA is controlled by the non-repetitive spacer elements in the pre-crRNA, which upon transcription along with the tracrRNA, directs the Cas9 nuclease to the protospacer:crRNA heteroduplex and induces double-strand breakage (DSB) formation. Additionally, the Cas9 nuclease cuts the DNA only if a specific sequence known as protospacer adjacent motif (PAM) is present immediately downstream of the protospacer sequence, whose canonical sequence in *S. pyogenes* is 5'-NGG-3', where N refers to any nucleotide. Later on, it has been demonstrated that the expression of a single chimeric crRNA:tracrRNA transcript, which normally is expressed as two different RNAs in the native type II CRISPR system, is sufficient to direct the Cas9 nuclease to sequence-specifically cleave target DNA sequences. By adapting the endogenous type II CRISPR/Cas system from *S. pyogenes* for use in mammalian cells, several groups have independently shown that RNA-guided Cas9 is able to efficiently introduce precise double stranded breaks at endogenous genomic loci in mammalian cells with high efficiencies and minimal off-target effects (Cong et al. 2013, Mali et al. 2013, Cho et al. 2013). In addition, several mutant forms of Cas9 nuclease have been developed to take advantage of their features for additional applications in genome engineering and transcriptional regulation. For instance, one mutant form of Cas9 nuclease functions as a nickase (Jinek et al. 2012), generating a break in complementary strand of DNA rather than both strands as with the wild-type Cas9. This allows repair of the DNA template using a high-fidelity pathway rather than NHEJ, which prevents formation of indels at the targeted locus, and possibly other locations in the genome to reduce possible off-target/toxicity effects while maintaining ability to undergo homologous recombination (Cong et al., 2013). Most recently, paired nicking has been shown to reduce off-target activity by 50- to 1,500 fold in cell lines and to facilitate gene knockout in mouse zygote without losing on-target cleavage efficiency (Ran et al., 2013).

Although RNA-guided endonucleases, such as the Cas9/CRISPR system appears to be an attractive approach for genetically engineering mammalian cells, the use thereof in primary cells, in particular in T-Cells, is significantly hurdled by the fact that:

T-cells are adversely affected by the introduction of DNA in their cytoplasm: high rate of apoptosis is observed when transforming cells with DNA vectors;

CRISPR system requires stable expression of Cas9 in the cells. However, prolonged expression of Cas9 in living cells may lead to chromosomal defects;

Specificity of current RNA-guided endonuclease is determined only by sequences comprising 11 nucleotides (N12-20NGG, where NGG represents the PAM), which makes it very difficult to identify target sequences in desired loci that are unique in the genome.

The present application aims to provide solutions to these limitations in order to efficiently implement RNA-guided endonucleases into T-cells.

SUMMARY OF THE INVENTION

The present invention discloses methods to engineer T cells, in particular allogeneic T cells obtainable from donors, to make them suitable for immunotherapy purposes, by using RNA-guided endonucleases such as Cas9/CRISPR.

The methods of the present invention more particularly allow the precise modification of the genome of T-cells relevant for immunotherapy by inactivating or replacing genes involved in MHC recognition and/or immune checkpoint proteins. In particular, they provide specific relevant targets sequences in the genome for the guide RNA to inactivate components of TCR without provoking death of the cells.

According to several preferred embodiments, the modified cells relevant for immunotherapy further comprise exogenous recombinant polynucleotides encoding single-chain and multi-subunit chimeric antigen receptor (CARs) for specific cell recognition. More particularly, modified T-cells for treating lymphoma are made available bearing CAR directed against CD19 antigen.

The present invention encompasses the isolated cells or cell lines comprising the genetic modifications set forth in the detailed description, examples and figures, as well as any of the proteins, polypeptides or vectors useful to implement RNA-guided endonucleases in T-cells.

As a result of the invention, modified T-cells can be used as therapeutic products, ideally as an "off the shelf" product, in methods for treating or preventing cancer, infections or auto-immune disease.

DETAILED DESCRIPTION OF THE INVENTION

Figure 1:
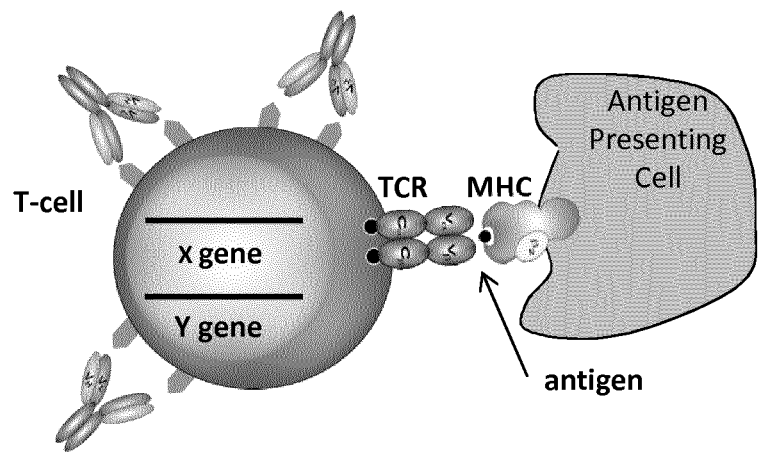
FIG. 1: Schematic representation of the normal relationship between T-cells and antigen presenting cell.
Figure 2:
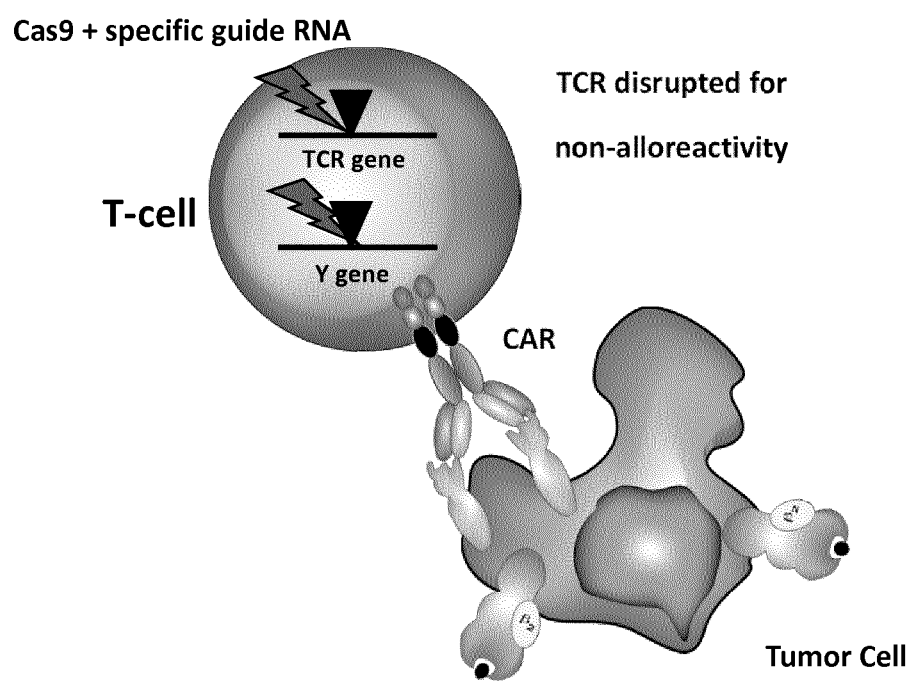
FIG. 2: Schematic representation of the genetically modified therapeutic T-cells according to the invention against the patient's tumor cells.
Figure 3:
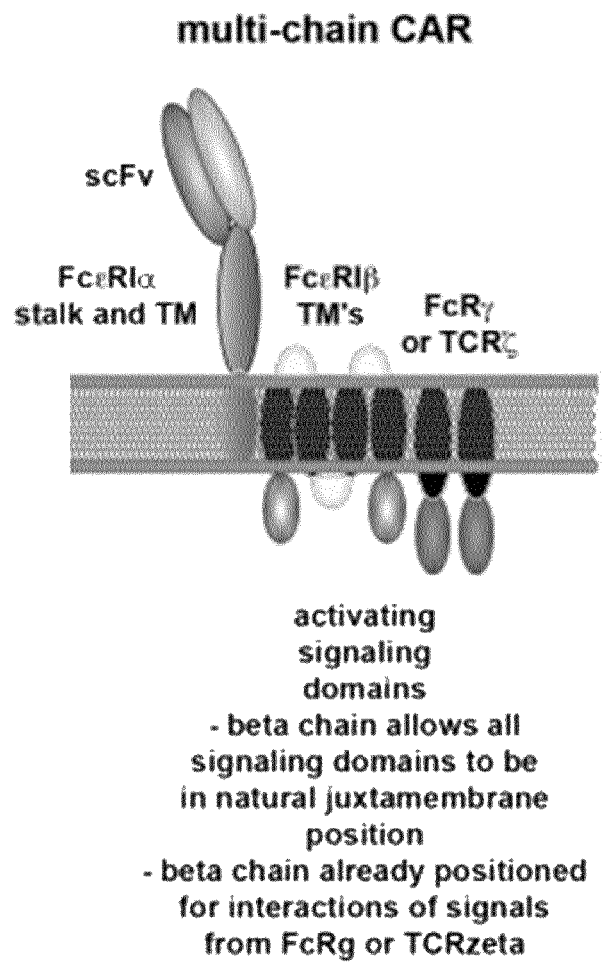
FIG. 3: Schematic representation of a multi-subunit CAR, which can introduced into the RNA guided endonuclease engineered T-cells according to the invention.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to methods for new adoptive immunotherapy strategies in treating cancer and infections.

As a main objective of the invention is the use of RNA-guided endonuclease, such as Cas9 to genetically modify T-cells for producing cells suitable in cell therapy.

In a first embodiment, the method of the invention concerns a method of preparing T-cells for immunotherapy comprising the step of:
  (a) Genetically modifying T-cells by introduction and/or expression into the cells of at least:
    a RNA-guided endonuclease; and
    a specific guide RNA that directs said endonuclease to at least one targeted locus in the T-cell genome
  (b) expanding the resulting cells.

By "RNA-guided endonuclease" is meant a polypeptide which endonuclease activity and specificity depend on its association with a RNA molecule. The full sequence of this RNA molecule or more generally a fragment of this RNA molecule, which is a sequence preferably longer than 8 nucleic acid bases, more preferably longer than 10 nucleic acid bases, even more preferably longer than 12 nucleic acid bases, has the ability to specify a target sequence in the genome. In general, this RNA molecule has the ability to hybridize said target sequence and to mediate the endonuclease activity of said endonuclease. An example of RNA-guided endonuclease is cas9 as part of the Cas9/CRISPR system.

Cas 9

Cas9, also named Csn1 (COG3513) is a large protein that participates in both crRNA biogenesis and in the destruction of invading DNA. Cas9 has been described in different bacterial species such as S. thermophilus (Sapranauskas, Gasiunas et al. 2011), Listeria innocua (Gasiunas, Barrangou et al. 2012; Jinek, Chylinski et al. 2012) and S. Pyogenes (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold) (Haft, Selengut et al. 2005; Makarova, Grishin et al. 2006).

By "Cas9" is also meant an engineered endonuclease or a homologue of Cas9 which is capable of processing target nucleic acid sequence. In particular embodiment, Cas9 can induce a cleavage in the nucleic acid target sequence which can correspond to either a double-stranded break or a single-stranded break. Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a S. pyogenes Cas9 endonuclease (COG3513—SEQ ID NO.3). In the frame aspects of the present invention, such Cas9 variants remain functional, i.e. they retain the capacity of processing a target nucleic acid sequence. Cas9 variant can also be homologues of S. pyogenes Cas9 which can comprise deletions from, or insertions or substitutions of, at least one residue within the amino acid sequence of S. pyogenes Cas9. Any combination of deletion, insertion, and substitution may also be made to arrive at the final construct, provided that the final construct possesses the desired activity, in particular the capacity of binding a guide RNA or nucleic acid target sequence.

RuvC/RNaseH motif includes proteins that show wide spectra of nucleolytic functions, acting both on RNA and DNA (RNaseH, RuvC, DNA transposases and retroviral integrases and PIWI domain of Argonaut proteins). In the present invention the RuvC catalytic domain of the Cas9 (SEQ ID NO. 4) protein can be characterized by the sequence motif: D-[I/L]-G-X-X-S-X-G-W-A, wherein X represents any one of the natural 20 amino acids and [I/L] represents isoleucine or leucine (SEQ ID NO: 1). In other terms, the present invention relates to Cas9 variant which comprises at least D-[I/L]-G-X-X-S-X-G-W-A sequence, wherein X represents any one of the natural 20 amino acids and [I/L] represents isoleucine or leucine (SEQ ID NO: 1).

HNH motif is characteristic of many nucleases that act on double-stranded DNA including colicins, restriction enzymes and homing endonucleases. The domain HNH (SMART ID: SM00507, SCOP nomenclature:HNH family) is associated with a range of DNA binding proteins, performing a variety of binding and cutting functions (Gorbalenya 1994; Shub, Goodrich-Blair et al. 1994). Several of the proteins are hypothetical or putative proteins of no well-defined function. The ones with known function are involved in a range of cellular processes including bacterial toxicity, homing functions in groups I and II introns and inteins, recombination, developmentally controlled DNA rearrangement, phage packaging, and restriction endonuclease activity (Dalgaard, Klar et al. 1997). These proteins are found in viruses, archaebacteria, eubacteria, and eukaryotes. Interestingly, as with the LAGLI-DADG (SEQ ID NO: 58) and the GIY-YIG motifs, the HNH motif is often associated with endonuclease domains of self-propagating elements like inteins, Group I, and Group II introns (Gorbalenya 1994; Dalgaard, Klar et al. 1997). The HNH domain can be characterized by the presence of a conserved Asp/His residue flanked by conserved His (amino-terminal) and His/Asp/Glu (carboxy-terminal) residues at some distance. A substantial number of these proteins can also have a CX2C motif on either side of the central Asp/His residue. Structurally, the HNH motif appears as a central hairpin of twisted β-strands, which are flanked on each side by an a helix (Kleanthous, Kuhlmann et al. 1999). The large HNH domain of Cas9 is represented by SEQ ID NO. 5. In the present invention, the HNH motif can be characterized by the sequence motif: Y-X-X-D-H-X-X-P-X-S-X-X-X-D-X-S, wherein X represents any one of the natural 20 amino acids (SEQ ID NO: 2). The present invention relates to a Cas9 variant which comprises at least Y-X-X-D-H-X-X-P-X-S-X-X-X-D-X-S sequence wherein X represents any one of the natural 20 amino acids (SEQ ID NO: 2).

This invention can be of particular interest to easily do targeted multiplex gene modifications and to create an inducible nuclease system by introduction of the guide RNA to the Cas9 cells. For the purpose of the present invention, the inventors have established that Cas9 protein can be divided into two separate split Cas9 RuvC and HNH domains which can process target nucleic acid sequence together or separately with the guide RNA.

Also the RuvC and HNH domains from different RNA guided endonucleases or Cas homologues may be assembled to improve nuclease efficiency or specificity. The domains from different species can be either split into two proteins or fused to each other to form a variant Cas protein. The Cas9 split system is deemed particularly suitable for an inducible method of genome targeting and to avoid the potential toxic effect of the Cas9 overexpression within the cell. Indeed, a first split Cas9 domain can be introduced into the cell, preferably by stably transforming said cell with a transgene encoding said split domain. Then, the complementary split part of Cas9 can be introduced into the cell, such that the two split parts reassemble into the cell to reconstitute a functional Cas9 protein at the desired time.

The reduction of the size of the split Cas9 compared to wild type Cas9 ease the vectorization and the delivery into the cell, for example, by using cell penetrating peptides. Re-arranging domains from different Cas proteins, allows to modulate the specificity and nuclease activity, for instance, by targeting PAM motifs that are slightly different from *S. pyogenes* Cas9

Split Cas9 System

The previous characterization of the RuvC and HNH domains has prompted the inventors to engineer Cas9 protein to create split Cas9 protein. Surprisingly, the inventors showed that these two split Cas9 could process together or separately the nucleic acid target. This observation allows developing a new Cas9 system using split Cas9 protein. Each split Cas9 domains can be prepared and used separately. Thus, this split system displays several advantages for vectorization and delivery of the RNA guided endonuclease in T-cells, allowing delivering a shorter and/or inactive protein, and is particularly suitable to induce genome engineering in T-cells at the desired time and thus limiting the potential toxicity of an integrated Cas9 nuclease.

By "Split Cas9" is meant here a reduced or truncated form of a Cas9 protein or Cas9 variant, which comprises either a RuvC or HNH domain, but not both of these domains. Such "Split Cas9" can be used independently with guide RNA or in a complementary fashion, like for instance, one Split Cas9 providing a RuvC domain and another providing the HNH domain. Different split RNA guided endonucleases may be used together having either RuvC and/or NHN domains.

Each Cas9 split domain can be derived from the same or from different Cas9 homologues. Many homologues of Cas9 have been identified in genome databases.

As a method of genome engineering the invention provides with the steps of:
 (a) selecting a target nucleic acid sequence, optionally comprising a PAM motif in the cell;
 (b) providing a guide RNA comprising a sequence complementary to the target nucleic acid sequence;
 (c) providing at least one split Cas9 domain;
 (d) introducing into the cell the guide RNA and said split Cas9 domain(s), such that split Cas9 domain(s) processes the target nucleic acid sequence in the cell.

Said Cas9 split domains (RuvC and HNH domains) can be simultaneously or sequentially introduced into the cell such that said split Cas9 domain(s) process the target nucleic acid sequence in the cell. Said Cas9 split domains and guide RNA can be introduced into the cell by using cell penetrating peptides or other transfection methods as described below.

In another aspect of the invention, only one split Cas9 domain, referred to as compact Cas9 is introduced into said cell. Indeed, surprisingly the inventors showed that the split Cas9 domain comprising the RuvC motif as described above is capable of cleaving a target nucleic acid sequence independently of split domain comprising the HNH motif. Thus, they could establish that the guideRNA does not need the presence of the HNH domain to bind to the target nucleic acid sequence and is sufficiently stable to be bound by the RuvC split domain. In a preferred embodiment, said split Cas9 domain alone is capable of nicking said target nucleic acid sequence.

Each split domain can be fused to at least one active domain in the N-terminal and/or C-terminal end, said active domain can be selected from the group consisting of: nuclease (e.g. endonuclease or exonuclease), polymerase, kinase, phosphatase, methylase, demethylase, acetylase, desacetylase, topoisomerase, integrase, transposase, ligase, helicase, recombinase, transcriptional activator (e.g. VP64, VP16), transcriptional inhibitor (e.g.; KRAB), DNA end processing enzyme (e.g. Trex2, Tdt), reporter molecule (e.g. fluorescent proteins, lacZ, luciferase).

HNH domain is responsible for nicking of one strand of the target double-stranded DNA and the RuvC-like RNaseH fold domain is involved in nicking of the other strand (comprising the PAM motif) of the double-stranded nucleic acid target (Jinek, Chylinski et al. 2012). However, in wild-type Cas9, these two domains result in blunt cleavage of the invasive DNA within the same target sequence (proto-spacer) in the immediate vicinity of the PAM (Jinek, Chylinski et al. 2012). Cas 9 can be a nickase and induces a nick event within different target sequences.

As non-limiting example, Cas9 or split Cas9 can comprise mutation(s) in the catalytic residues of either the HNH or RuvC-like domains, to induce a nick event within different target sequences. As non-limiting example, the catalytic residues of the Cas9 protein are those corresponding to amino acids D10, D31, H840, H868, N882 and N891 or aligned positions using CLUSTALW method on homologues of Cas Family members. Any of these residues can be replaced by any other amino acids, preferably by alanine residue. Mutation in the catalytic residues means either substitution by another amino acids, or deletion or addition of amino acids that induce the inactivation of at least one of the catalytic domain of cas9. (cf. In a particular embodiment, Cas9 or split Cas9 may comprise one or several of the above mutations. In another particular embodiment, split Cas9 comprises only one of the two RuvC and HNH catalytic domains. In the present invention, Cas9 from different species, Cas9 homologues, Cas9 engineered and functional variant thereof can be used. The invention envisions the use of any RNA guided endonuclease or split RNA guided endonucleases variants to perform nucleic acid cleavage in a genetic sequence of interest.

Preferably, said Cas9 variants have an amino acid sequence sharing at least 70%, preferably at least 80%, more preferably at least 90%, and even more preferably 95% identity with Cas9 of *S. Pyogenes* (COG3513—SEQ ID NO.3).

In another aspect of the present invention, Cas9 or split Cas9 lack of endonucleolytic activity. The resulting Cas9 or split Cas9 is co-expressed with guide RNA designed to comprises a complementary sequence of the target nucleic acid sequence. Expression of Cas9 lacking endonucleolytic activity yields to specific silencing of the gene of interest. This system is named CRISPR interference (CRISPRi) (Qi, Larson et al. 2013). By silencing, it is meant that the gene of interest is not expressed in a functional protein form. The silencing may occur at the transcriptional or the translational step. According to the present invention, the silencing may occur by directly blocking transcription, more particularly by blocking transcription elongation or by targeting key cis-acting motifs within any promoter, sterically blocking the association of their cognate trans-acting transcription factors. The Cas9 lacking endonucleolytic activity comprises both non-functional HNH and RuvC domains. In particular, the Cas9 or split Cas9 polypeptide comprises inactivating mutations in the catalytic residues of both the RuvC-like and HNH domains. For example, the catalytic residues required for cleavage Cas9 activity can be D10, D31, H840, H865, H868, N882 and N891 of Cas9 of *S. Pyogenes* (COG3513—SEQ ID NO.3) or aligned positions using CLUSTALW method on homologues of Cas Family members. The residues comprised in HNH or RuvC motifs can be those described in the above paragraph. Any of these residues can be replaced by any one of the other amino acids, preferably by alanine residue. Mutation in the catalytic residues means either substitution by another amino acids, or deletion or addition of amino acids that induce the inactivation of at least one of the catalytic domain of cas9.

In another particular embodiment, Cas9 or each split domains can be fused to at least one active domain in the N-terminal and/or C-terminal end. Said active domain can be selected from the group consisting of: nuclease (e.g. endonuclease or exonuclease), polymerase, kinase, phosphatase, methylase, demethylase, acetylase, desacetylase, topoisomerase, integrase, transposase, ligase, helicase, recombinase, transcriptional activator (e.g. VP64, VP16), transcriptional inhibitor (e.g.; KRAB), DNA end processing enzyme (e.g. Trex2, Tdt), reporter molecule (e.g. fluorescent proteins, lacZ, luciferase).

Inducible Nuclease Activity for the RNA Guided Endonuclease/Guided RNA System

Given the potential toxicity of the RNA guided endonuclease within the T-cells, due to possible unspecific interactions with various RNAs in the cell and expectable off-site targeting, the inventors have sought for solutions to induce the nuclease activity of the RNA-guided endonuclease transiently, ideally during the life-span of the guide RNA into the cells.

As a primary solution, the RNA-guided endonuclease can be expressed under a stabilized or inactive form, which is made active upon activation by an enzyme produced by the T-cell or destabilization of its polypeptide structure inside the T-cell. Conditional protein stability can be obtained for instance by fusion of the endonuclease to a stabilizing/destabilizing protein based, as a non-limiting example, on the FKBP/rapamycin system, where protein conformational change induced by a small molecule.

Chemical or light induced dimerization of a protein partner fused to the endonuclease protein can also be used to lock or unlock the endonuclease.

In the situation where the RNA guided endonuclease is split in two polypeptides as suggested before, each split can be fused to a partner protein. Both partner proteins will dimerize upon addition of a small molecule and reconstitute, in living cells, an active endonuclease. Such systems can be based, as non-limiting example, on the use of FKBB/FRB as dimerization partners and rapamycin as a small molecule. As another example, protein that can undergo a major conformational change upon binding to a small molecule or metabolite inserted in the endonuclease protein (1 polypeptide chain composed of 2 "splits"). Binding (or not) of the small molecule will switch the Cas9 between an active and inactive conformation. Such systems can be based, as non-limiting example, on the use of calmodulin and Ca2+.

Each half of the split endonuclease can also be fused to a partner protein sensitive to light. Such systems can rely, as non-limiting example, on blue light with the Cryptochrome 2 (CRY2) and CIB1 as fusion partners or on ultraviolet light with the ultraviolet-B photoreceptor UVR8 and COP1 fusion partners. Both light and chemical may also be combined by using, for instance, the Phytochrome B and PIF6 partners (red light association, far red light dissociation) and an exogenous PCB chromophore.

Guide RNA

The method of the present invention comprises providing an engineered guide RNA. Guide RNA corresponds to a nucleic acid sequence comprising a complementary sequence. Preferably, said guide RNA correspond to a crRNA and tracrRNA which can be used separately or fused together.

In natural type II CRISPR system, the CRISPR targeting RNA (crRNA) targeting sequences are transcribed from DNA sequences known as protospacers. Protospacers are clustered in the bacterial genome in a group called a CRISPR array. The protospacers are short sequences (~20 bp) of known foreign DNA separated by a short palindromic repeat and kept like a record against future encounters. To create the crRNA, the CRISPR array is transcribed and the RNA is processed to separate the individual recognition sequences between the repeats. The spacer-containing CRISPR locus is transcribed in a long pre-crRNA. The processing of the CRISPR array transcript (pre-crRNA) into individual crRNAs is dependent on the presence of a trans-activating crRNA (tracrRNA) that has sequence complementary to the palindromic repeat. The tracrRNA hybridizes to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9 and form the Cas9-tracrRNA:crRNA complex. Engineered crRNA with tracrRNA is capable of targeting a selected nucleic acid sequence, obviating the need of RNase III and the crRNA processing in general (Jinek, Chylinski et al. 2012).

In the present invention, crRNA is engineered to comprise a sequence complementary to a portion of a target nucleic acid such that it is capable of targeting, preferably cleaving the target nucleic acid sequence. In a particular embodiment, the crRNA comprises a sequence of 5 to 50 nucleotides, preferably 12 nucleotides which is complementary to the target nucleic acid sequence. In a more particular embodiment, the crRNA is a sequence of at least 30 nucleotides which comprises at least 10 nucleotides, preferably 12 nucleotides complementary to the target nucleic acid sequence.

In another aspect, crRNA can be engineered to comprise a larger sequence complementary to a target nucleic acid.

Indeed, the inventors showed that the RuvC split Cas9 domain is able to cleave the target nucleic acid sequence only with a guide RNA. Thus, the guide RNA can bind the target nucleic acid sequence in absence of the HNH split Cas9 domain. The crRNA can be designed to comprise a larger complementary sequence, preferably more than 20 bp, to increase the annealing between DNA-RNA duplex without the need to have the stability effect of the HNH split domain binding. Thus, the crRNA can comprise a complementary sequence to a target nucleic acid sequence of more than 20 bp. Such crRNA allow increasing the specificity of the Cas9 activity.

The crRNA may also comprise a complementary sequence followed by 4-10 nucleotides on the 5'end to improve the efficiency of targeting (Cong, Ran et al. 2013; Mali, Yang et al. 2013). In preferred embodiment, the complementary sequence of the crRNA is followed in 3'end by a nucleic acid sequence named repeat sequences or 3'extension sequence.

Co-expression of several crRNA with distinct complementary regions to two different genes targeted both genes can be used simultaneously. Thus, in particular embodiment, the crRNA can be engineered to recognize different target nucleic acid sequences simultaneously.

In this case, same crRNA comprises at least two distinct sequences complementary to a portion of the different target nucleic acid sequences. In a preferred embodiment, said complementary sequences are spaced by a repeat sequence.

As a further embodiment of the present invention, said guide RNA is born by a peptide nucleic acid (PNA) or Locked Nucleic Acid (LNA), in particular to improve stability of said guide RNA in the T-cells.

PAM Motif

Any potential selected target nucleic acid sequence in the present invention may have a specific sequence on its 3' end, named the protospacer adjacent motif or protospacer associated motif (PAM). The PAM is present in the targeted nucleic acid sequence but not in the crRNA that is produced to target it. Preferably, the proto-spacer adjacent motif (PAM) may correspond to 2 to 5 nucleotides starting immediately or in the vicinity of the proto-spacer at the leader distal end. The sequence and the location of the PAM vary among the different systems. PAM motif can be for examples NNAGAA, NAG, NGG, NGGNG, AWG, CC, CC, CCN, TCN, TTC as non-limiting examples (Shah S A, RNA biology 2013). Different Type II systems have differing PAM requirements. For example, the *S. pyogenes* system requires an NGG sequence, where N can be any nucleotides. *S. thermophilus* Type II systems require NGGNG (Horvath and Barrangou 2010) and NNAGAAW (Deveau, Barrangou et al. 2008), while different *S. mutant* systems tolerate NGG or NAAR (Van der Ploeg 2009). PAM is not restricted to the region adjacent to the proto-spacer but can also be part of the proto-spacer (Mojica, Diez-Villasenor et al. 2009). In a particular embodiment, the Cas9 protein can be engineered not to recognize any PAM motif or to recognize a non-natural PAM motif. In this case, the selected target sequence may comprise a smaller or a larger PAM motif with any combinations of amino acids. In a preferred embodiment, the selected target sequence comprise a PAM motif which comprises at least 3, preferably, 4, more preferably 5 nucleotides recognized by the Cas9 variant according to the present invention.

Coexpression of several crRNA with distinct complementary regions to two different genes targeted both genes can be used simultaneously. Thus, in particular embodiment, the crRNA can be engineered to recognize different target nucleic acid sequences simultaneously. In this case, same crRNA comprises at least two distinct sequences complementary to a portion of the different target nucleic acid sequences. In a preferred embodiment, said complementary sequences are spaced by a repeat sequence.

The crRNA according to the present invention can also be modified to increase its stability of the secondary structure and/or its binding affinity for Cas9. In a particular embodiment, the crRNA can comprise a 2',3'-cyclic phosphate. The 2',3'-cyclic phosphate terminus seems to be involved in many cellular processes i.e. tRNA splicing, endonucleolytic cleavage by several ribonucleases, in self-cleavage by RNA ribozyme and in response to various cellular stress including accumulation of unfolded protein in the endoplasmatic reticulum and oxidative stress (Schutz, Hesselberth et al. 2010). The inventors have speculated that the 2',3'-cyclic phosphate enhances the crRNA stability or its affinity/specificity for Cas9. Thus, the present invention relates to the modified crRNA comprising a 2',3'-cyclic phosphate, and the methods for genome engineering based on the CRISPR/cas system (Jinek, Chylinski et al. 2012; Cong, Ran et al. 2013; Mali, Yang et al. 2013) using the modified crRNA.

The guide RNA may also comprise a Trans-activating CRISPR RNA (TracrRNA). Trans-activating CRISPR RNA according to the present invention are characterized by an anti-repeat sequence capable of base-pairing with at least a part of the 3' extension sequence of crRNA to form a tracrRNA:crRNA also named guide RNA (gRNA). TracrRNA comprises a sequence complementary to a region of the crRNA. A guide RNA comprising a fusion of crRNA and tracrRNA that forms a hairpin that mimics the tracrRNA-crRNA complex (Jinek, Chylinski et al. 2012; Cong, Ran et al. 2013; Mali, Yang et al. 2013) can be used to direct Cas9 endonuclease-mediated cleavage of target nucleic acid. The guide RNA may comprise two distinct sequences complementary to a portion of the two target nucleic acid sequences, preferably spaced by a repeat sequence.

Homologous Recombination

Endonucleolytic breaks are known to stimulate the rate of homologous recombination. Therefore, as another preferred embodiment, the present invention relates to a method for inducing homologous gene targeting in the nucleic acid target sequence by using a RNA guided endonuclease. This method can further comprise the step of providing an exogeneous nucleic acid to the cell (e.g. donor DNA) comprising at least a sequence homologous to a portion of the target nucleic acid sequence, such that homologous recombination occurs between the target nucleic acid sequence and said exogeneous nucleic acid.

In particular embodiments, said exogenous nucleic acid comprises first and second portions which are homologous to region 5' and 3' of the target nucleic acid sequence, respectively. Said exogenous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. Preferably, homologous sequences of at least 50 bp, preferably more than 100 bp and more preferably more than 200 bp are used within said donor matrix. Therefore, the homologous sequence is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

Depending on the location of the target nucleic acid sequence wherein break event has occurred, such exogenous nucleic acid can be used to knock-out a gene, e.g. when exogenous nucleic acid is located within the open reading frame of said gene, or to introduce new sequences or genes of interest. Sequence insertions by using such exogenous nucleic acid can be used to modify a targeted existing gene, by correction or replacement of said gene (allele swap as a non-limiting example), or to up- or down-regulate the expression of the targeted gene (promoter swap as non-limiting example), said targeted gene correction or replacement.

Delivery Methods

The methods of the invention involve introducing molecule of interest such as guide RNA (crRNA, tracrRNa, or fusion guide RNA), split Cas9, Cas9, exogenous nucleic acid, DNA end-processing enzyme into a cell. Guide RNA, split Cas9, Cas9, exogenous nucleic acid, DNA end-processing enzyme or others molecules of interest may be synthesized in situ in the cell as a result of the introduction of polynucleotides, preferably transgenes, comprised in vector encoding RNA or polypeptides into the cell. Alternatively, the molecule of interest could be produced outside the cell and then introduced thereto.

The inventors have considered any means known in the art to allow delivery inside cells or subcellular compartments of agents/chemicals and molecules (proteins and nucleic acids) can be used including liposomal delivery means, polymeric carriers, chemical carriers, lipoplexes, polyplexes, dendrimers, nanoparticles, emulsion, natural endocytosis or phagocytose pathway as non-limiting examples, as well as physical methods such as electroporation.

As a preferred embodiment of the invention, polynucleotides encoding the RNA guided endonuclease of the present invention are transfected under mRNA form, which is introduced directly into the cells, for example by electroporation. The inventors have determined different optimal conditions for mRNA electroporation in T-cell displayed in Table 1. The inventor used the cytoPulse technology which allows, by the use of pulsed electric fields, to transiently permeabilize living cells for delivery of material into the cells. The transfection efficiency with minimal mortality. Basically, the first high electric field pulses allow pore formation, while subsequent lower electric field pulses allow to move the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

TABLE 1

Different cytopulse programs used to determine the minimal voltage required for electroporation in PBMC derived T-cells.

| Cytopulse program | Group 1 | | | | Group 2 | | | | Group 3 | | | |
|---|---|---|---|---|---|---|---|---|---|---|---|---|
| | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 | technology, based on the use of PulseAgile (Harvard Apparatus, Holliston, Mass. 01746 USA) electroporation waveforms grants the precise control of pulse duration, intensity as well as the interval between pulses (U.S. Pat. No. 6,010,613 and WO2004083379). All these parameters can be modified in order to reach the best conditions for high Viral Transduction According to the present invention, the use of viral vectors as defined hereafter for transduction of the nucleic acids encoding the RNA-guided endonucleases and/or the transcripts to be used as guide RNA was found to be a possible alternative to the previous means of transfection.

Methods for viral transduction are well known in the art. However, such methods may encounter some limitations in the present situation due to the stable integration of the retroviral or lentiviral vectors in the T-cells genome and the resulting expression of the endonuclease over a long period of time. This may have deleterious effects on the T-cells depending on the level of specificity conferred by the RNA guide.

Pseudo-Transduction Using Viral Encapsidation of RNA-Guided Endonuclease

Given some of the disadvantages of existing means and materials to deliver RNA-guided endonucleases to their sites of action in T-cells, alternative delivery methods have been sought by the inventors, in particular delivery methods where the RNA-guided endonucleases is introduced under polypeptide form by fusing said polypeptide viral components. As an example, the RNA-guided endonucleases can be fused to proteins of the HIV pre-integration complex, such as Vpr or Vpx. Accordingly, RNA-guided endonucleases under polypeptide form can act upon a specific target in the host cell genome as soon as they are released into the cell following virus entry and decapsulation.

For therapeutic application, where the use of the above retroviral components may raise issues, because they are "helper proteins" for opportunistic viral infections, an alternative could be unexpectedly found by the inventors. They have observed that RNA-guided endonucleases, in particular Cas9 could be incorporated into lentiviral vector particles during virion assembly and that such 'self' incorporated endonucleases are sufficient to act so as to modify a target genome following infection of a target cell by such a virus vector.

In accordance with this aspect of the invention, there is provided a method of genome engineering involving one or several of the steps of:
 a) assembling at least one virus vector in the presence of an endonuclease; said endonuclease being preferably not fused with any lentiviral component
 b) bringing at least one target cell into contact with said virus vector,
 c) wherein following internalization of said virus vector by said target cell, said nuclease recognizes and cleaves at least one specific target in the genome of said at least one target cell.

In accordance with the present invention viral vectors include those derived from a virus such as a retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). The terms "viral vector" or "vector" refers to a modified virus particle which can be used to introduce a nucleic acid molecule and/or a peptide or other molecule into a target cell.

The inventors have shown that following transfer into the cell cytoplasm, the RNA-guided endonuclease retains its activity and can readily associate with the guide RNA. Said guide RNA can also be encapsidated during virion assembly and thereby simultaneously released in the T-cells cytoplasm.

In accordance with a further aspect of the present invention the virus vector is a Lentiviral or retroviral based vector (LV), which are preferably non-integrative. LVs are replication defective viral particles which comprise an inner protein core surrounding the genetic material of the virus, generally called the nucleocapsid core and an outer lipid membrane. These replication defective viral particles are assembled by expressing proteins encoded by the lentiviral gag and pol genes in packaging cells. The gag and pol genes encode polyproteins and a protease that processes these polyproteins into individual components of the virus particle.

A NLS, an amino acid sequence which acts to drive the protein to the cell nucleus through the Nuclear Pore Complex can be fused to the RNA guided endonuclease in order to improve its delivery efficiency. Typically, a NLS consists of one or more short sequences of positively charged amino acids such as lysines or arginines such as those from the known proteins SV40 large T antigen—PKKKRKV—(SEQ ID NO: 59), nucleoplasmin—KR[PAATKKAGQA]KKKK—(SEQ ID NO: 60), p54—RIRKKLR—(SEQ ID NO: 61), SOX9—PRRRK—(SEQ ID NO: 62), NS5A—PPRKKRTVV—(SEQ ID NO: 63).

Independently from the present use of RNA-guided endonucleases according to the invention, the above method of viral encapsidation can be expanded to other types of rare-cutting endonucleases, such as TAL-nucleases, Zing Finger nucleases or homing endonucleases, with respect to any types of cells that can be infected by viral vectors.

Cell-Penetrating Peptides Delivery Methods

Further delivery methods have been investigated by the inventors as part of the present invention, in particular the use of cell penetrating peptides (CPP) for introducing the RNA guide and/or the RNA guided endonuclease into the T-cells.

Accordingly, the method of the invention may comprise a step of preparing composition comprising a cell penetrating peptide linked to the RNA guide and/or the RNA guided endonuclease. Said CPP, preferably N-terminal or C-terminal end of CPP can also be associated with the molecules. This association can be covalent or non-covalent. CPPs can be subdivided into two main classes, the first requiring chemical linkage with the molecule and the second involving the formation of stable, non-covalent complexes. Covalent bonded CPPs form a covalent conjugate by chemical cross-linking (e.g. disulfide bond) or by cloning followed by expression of a CPP-RNA guided endonuclease fusion protein. In a preferred embodiment, said CPP bears a pyrydil disulfide function such that the thiol modified molecule forms a disulfide bond with the CPP. Said disulfide bond can be cleaved in particular in a reducing environment such as cytoplasm. Non-covalent bonded CPPs are preferentially amphipathic peptide Although definition of CPPs is constantly evolving, they are generally described as short peptides of less than 35 amino acids either derived from proteins or from chimeric sequences, which are capable of transporting polar hydrophilic biomolecules across cell membrane in a receptor independent manner. CPP can be cationic peptides, peptides having hydrophobic sequences, amphipatic peptides, peptides having proline-rich and anti-microbial sequence, and chimeric or bipartite peptides (Pooga and Langel 2005). In a particular embodiment, cationic CPP can comprise multiple basic of cationic CPPs (e.g., arginine and/or lysine). Preferably, CCP are amphipathic and possess a net positive charge. CPPs are able to penetrate biological membranes, to trigger the movement of various biomolecules across cell membranes into the cytoplasm and to improve their intracellular routing, thereby facilitating interactions with the target. Examples of CPP can include: Tat, a nuclear transcriptional activator protein which is a 101 amino acid protein required for viral replication by human immunodeficiency virus type 1 (HIV-1), penetratin, which corresponds to the third helix of the homeoprotein Antennapedia in Drosophilia, Kaposi fibroblast growth factor (FGF) signal peptide sequence, integrin β3 signal peptide sequence; Guanine rich-molecular transporters, MPG, pep-1, sweet arrow peptide, dermaseptins, transportan, pVEC, Human calcitonin, mouse prion protein (mPrPr), polyarginine peptide Args sequence, VP22 protein from Herpes Simplex Virus, antimicrobial peptides Buforin I and SynB (US2013/0065314). New variants of CPPs can combine different transduction domains.

Non Alloreactive T Cells:

T cell receptors (TCR) are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD. However, TCR disruption generally results in the elimination of the CD3 signaling component and alters the means of further T cell expansion.

As one major objective of the present invention is the use of RNA guided endonuclease as previously described in a method for engineering non-alloreactive T-cells, for their use in immunotherapy.

This method more particularly comprises the steps of modifying T-cells as previously described by inactivating at least one component of the T-cell receptor (TCR) by using a RNA guided endonuclease associated with a specific guide RNA.

Engraftment of allogeneic T-cells is possible by inactivating at least one gene encoding a TCR component. TCR is rendered not functional in the cells by inactivating TCR alpha gene and/or TCR beta gene(s). TCR inactivation in allogeneic T-cells aims to prevent or reduce GvHD.

By inactivating a gene it is intended that the gene of interest is not expressed in a functional protein form. In particular embodiments, the genetic modification of the method relies on the expression, in provided cells to engineer, of the RNA guided endonuclease such that same catalyzes cleavage in one targeted gene thereby inactivating said targeted gene. The nucleic acid strand breaks caused by the endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

The inventors have determined appropriate target sequences within the 3 exons encoding TCR, allowing a significant reduction of toxicity, while retaining cleavage efficiency. The preferred target sequences are noted in Table 2 (+ for lower ratio of TCR negative cells, ++ for intermediate ratio, +++ for higher ratio).

TABLE 2 appropriate target sequences for the guide RNA using Cas9 in T-cells

| Exon TCR | Position | Strand | Target genomic sequence | SEQ ID | efficiency |
|---|---|---|---|---|---|
| Ex1 | 78 | −1 | GAGAATCAAAATCGGTGAATAGG | 6 | +++ |
| Ex3 | 26 | 1 | TTCAAAACCTGTCAGTGATTGGG | 7 | +++ |
| Ex1 | 153 | 1 | TGTGCTAGACATGAGGTCTATGG | 8 | +++ |
| Ex3 | 74 | −1 | CGTCATGAGCAGATTAAACCCGG | 9 | +++ |
| Ex1 | 4 | −1 | TCAGGGTTCTGGATATCTGTGGG | 10 | +++ |
| Ex1 | 5 | −1 | GTCAGGGTTCTGGATATCTGTGG | 11 | +++ |

TABLE 2-continued appropriate target sequences
for the guide RNA using Cas9 in T-cells

| Exon TCR | Position | Strand | Target genomic sequence | SEQ ID | efficiency |
|---|---|---|---|---|---|
| Ex3 | 33 | -1 | TTCGGAACCCAATCACTGACAGG | 12 | +++ |
| Ex3 | 60 | -1 | TAAACCCGGCCACTTTCAGGAGG | 13 | +++ |
| Ex1 | 200 | -1 | AAAGTCAGATTTGTTGCTCCAGG | 14 | ++ |
| Ex1 | 102 | 1 | AACAAATGTGTCACAAAGTAAGG | 15 | ++ |
| Ex1 | 39 | -1 | TGGATTTAGAGTCTCTCAGCTGG | 16 | ++ |
| Ex1 | 59 | -1 | TAGGCAGACAGACTTGTCACTGG | 17 | ++ |
| Ex1 | 22 | -1 | AGCTGGTACACGGCAGGGTCAGG | 18 | ++ |
| Ex1 | 21 | -1 | GCTGGTACACGGCAGGGTCAGGG | 19 | ++ |
| Ex1 | 28 | -1 | TCTCTCAGCTGGTACACGGCAGG | 20 | ++ |
| Ex3 | 25 | 1 | TTTCAAAACCTGTCAGTGATTGG | 21 | ++ |
| Ex3 | 63 | -1 | GATTAAACCCGGCCACTTTCAGG | 22 | ++ |
| Ex2 | 17 | -1 | CTCGACCAGCTTGACATCACAGG | 23 | ++ |
| Ex1 | 32 | -1 | AGAGTCTCTCAGCTGGTACACGG | 24 | ++ |
| Ex1 | 27 | -1 | CTCTCAGCTGGTACACGGCAGGG | 25 | ++ |
| Ex2 | 12 | 1 | AAGTTCCTGTGATGTCAAGCTGG | 26 | ++ |
| Ex3 | 55 | 1 | ATCCTCCTCCTGAAAGTGGCCGG | 27 | ++ |
| Ex3 | 86 | 1 | TGCTCATGACGCTGCGGCTGTGG | 28 | ++ |
| Ex1 | 146 | 1 | ACAAAACTGTGCTAGACATGAGG | 29 | + |
| Ex1 | 86 | -1 | ATTTGTTTGAGAATCAAAATCGG | 30 | + |
| Ex2 | 3 | -1 | CATCACAGGAACTTTCTAAAAGG | 31 | + |
| Ex2 | 34 | 1 | GTCGAGAAAAGCTTTGAAACAGG | 32 | + |
| Ex3 | 51 | -1 | CCACTTTCAGGAGGAGGATTCGG | 33 | + |
| Ex3 | 18 | -1 | CTGACAGGTTTTGAAAGTTTAGG | 34 | + |
| Ex2 | 43 | 1 | AGCTTTGAAACAGGTAAGACAGG | 35 | + |
| Ex1 | 236 | -1 | TGGAATAATGCTGTTGTTGAAGG | 36 | + |
| Ex1 | 182 | 1 | AGAGCAACAGTGCTGTGGCCTGG | 37 | + |
| Ex3 | 103 | 1 | CTGTGGTCCAGCTGAGGTGAGGG | 38 | + |
| Ex3 | 97 | 1 | CTGCGGCTGTGGTCCAGCTGAGG | 39 | + |
| Ex3 | 104 | 1 | TGTGGTCCAGCTGAGGTGAGGGG | 40 | + |
| Ex1 | 267 | 1 | CTTCTTCCCCAGCCCAGGTAAGG | 41 | + |
| Ex1 | 15 | -1 | ACACGGCAGGGTCAGGGTTCTGG | 42 | + |
| Ex1 | 177 | 1 | CTTCAAGAGCAACAGTGCTGTGG | 43 | + |
| Ex1 | 256 | -1 | CTGGGGAAGAAGGTGTCTTCTGG | 44 | + |
| Ex3 | 56 | 1 | TCCTCCTCCTGAAAGTGGCCGGG | 45 | + |
| Ex3 | 80 | 1 | TTAATCTGCTCATGACGCTGCGG | 46 | + |
| Ex3 | 57 | -1 | ACCCGGCCACTTTCAGGAGGAGG | 47 | + |
| Ex1 | 268 | 1 | TTCTTCCCCAGCCCAGGTAAGGG | 48 | + |

TABLE 2-continued appropriate target sequences
for the guide RNA using Cas9 in T-cells

| Exon TCR | Position | Strand | Target genomic sequence | SEQ ID | efficiency |
|---|---|---|---|---|---|
| Ex1 | 266 | -1 | CTTACCTGGGCTGGGGAAGAAGG | 49 | + |
| Ex1 | 262 | 1 | GACACCTTCTTCCCCAGCCCAGG | 50 | + |
| Ex3 | 102 | 1 | GCTGTGGTCCAGCTGAGGTGAGG | 51 | + |
| Ex3 | 51 | 1 | CCGAATCCTCCTCCTGAAAGTGG | 52 | + |

Method of Engineering Drug-Resistant T-Cells:

To improve cancer therapy and selective engraftment of allogeneic T-cells, drug resistance can be conferred to the engineered T-cells to protect them from the toxic side effects of chemotherapy or immunosuppressive agents. Indeed, the inventors have observed that most patients were treated with chemotherapy and immune depleting agents as a standard of care, prior to trials involving T-cell immunotherapy. Also they found that they could take advantage of these treatments to help the selection of the engineered T-cells, either by adding chemotherapy drugs in culture media for expansion of the cells ex-vivo prior to treatment, or by obtaining a selective expansion of the engineered T-cells in-vivo in patients under chemotherapy or immunosuppressive treatments.

Also the drug resistance of T-cells also permits their enrichment in or ex vivo, as T-cells which express the drug resistance gene, will survive and multiply relative to drug sensitive cells. In particular, the present invention relates to a method of engineering allogeneic and drug resistance T-cells resistant for immunotherapy comprising:
  (a) Providing a T-cell;
  (b) Selecting at least one drug;
  (c) Modifying T-cell to confer drug resistance to said T-cell;
  (d) Expanding said engineered T-cell in the presence of said drug, and optionally
The preceding steps may be combined with the steps previously described of:
  (e) Modifying said T-cell by inactivating at least one gene encoding a T-cell receptor (TCR) component;
  (f) Sorting the transformed T-cells, which do not express TCR on their cell surface;

Thus, according to one aspect of the present invention, the method comprises the step of inactivating at least one gene encoding a T-Cell Receptor (TCR) component, while further modifying said T-cell to confer a resistance to a drug, more particularly a chemotherapy agent. The resistance to a drug can be conferred to a T-cell by expressing a drug resistance gene. Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell. Said drug resistance gene can be expressed in the cell either by introducing a transgene encoding said gene into the cell or by integrating said drug resistance gene into the genome of the cell by homologous recombination.

The resistance to a drug can be conferred to a T-cell by inactivating one or more gene(s) responsible for the cell's sensitivity to the drug (drug sensitizing gene(s)), such as the hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Another example if the inactivation of the CD3 normally expressed at the surface of the T-cell can confer resistance to anti-CD3 antibodies such as teplizumab.

Otherwise, said drug resistance can be conferred to the T-cell by the expression of at least one drug resistance gene. Said drug resistance gene refers to a nucleic acid sequence that encodes "resistance" to an agent, such as a chemotherapeutic agent (e.g. methotrexate). In other words, the expression of the drug resistance gene in a cell permits proliferation of the cells in the presence of the agent to a greater extent than the proliferation of a corresponding cell without the drug resistance gene. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, and the like.

Several drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

One example of drug resistance gene can also be a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 ((Schweitzer, Dicker et al. 1990); International application WO94/24277; U.S. Pat. No. 6,642,043).

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dideazaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (NP_000875.2) that lead to a significantly increased resistance to IMPDH inhibitor. The mutations are preferably at positions T333 and/or S351 (Yam, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue.

Another drug resistance gene is the mutant form of calcineurin. Calcineurin (PP2B) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as 1L2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. Correspondence of amino acid positions described herein is frequently expressed in terms of the positions of the amino acids of the form of wild-type human calcineurin heterodimer (GenBank: ACX34092.1).

In another particular embodiment, said mutant form can comprise at least one mutated amino acid of the wild type calcineurin heterodimer b at positions: V120, N123, L124 or K125, preferably double mutations at positions L124 and K125. Correspondence of amino acid positions described herein is frequently expressed in terms of the positions of the amino acids of the form of wild-type human calcineurin heterodimer b polypeptide (GenBank: ACX34095.1).

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, Kurpad et al. 1999). In a particular embodiment, AGT mutant form can comprise a mutated amino acid of the wild type AGT position P140 (UniProtKB: P16455).

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (NP_000918).

Drug resistance gene can also be cytotoxic antibiotics, such as ble gene or mcrA gene. Ectopic expression of ble gene or mcrA in an immune cell gives a selective advantage when exposed to the chemotherapeutic agent, respectively the bleomycine or the mitomycin C.

With respect to the immunosuppressive agents, the present invention provides the possible optional steps of:
(a) Providing a T-cell, preferably from a cell culture or from a blood sample;
(b) Selecting a gene in said T-cell expressing a target for an immunosuppressive agent;
(c) Introducing into said T-cell RNA guided endonuclease able to selectively inactivate by DNA cleavage, preferably by double-strand break, said gene encoding a target for said immunosuppressive agent,
(d) Expanding said cells, optionally in presence of said immunosuppressive agent.

In a more preferred embodiment, said method comprises to inactivate a component of the T-cell receptor (TCR).

An immunosuppressive agent is an agent that suppresses immune function by one of several mechanisms of action. In other words, an immunosuppressive agent is a role played by a compound which is exhibited by a capability to diminish the extent and/or voracity of an immune response. As non-limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non limiting examples, targets for immunosuppressive agent can be a receptor for an immunosuppressive agent such as: CD52, glucocorticoid receptor (GR), a FKBP family gene member and a cyclophilin family gene member.

In immunocompetent hosts, allogeneic cells are normally rapidly rejected by the host immune system. It has been demonstrated that, allogeneic leukocytes present in non-irradiated blood products will persist for no more than 5 to 6 days. (Boni, Muranski et al. 2008). Thus, to prevent rejection of allogeneic cells, the host's immune system must be effectively suppressed. Glucocorticoidsteroids are widely used therapeutically for immunosuppression (Coutinho and Chapman 2011). This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H, is a humanized monoclonal antibody targeting CD52, a 12 amino acid glycosylphosphatidyl-inositol-(GPI) linked glycoprotein (Waldmann and Hale 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

As a preferred embodiment of the above steps, said gene of step (b), specific for an immunosuppressive treatment, is CD52, and the immunosuppressive treatment of step (d) comprises a humanized antibody targeting CD52 antigen. As another embodiment, said gene of step (b), specific for an immunosuppressive treatment, is a glucocorticoid receptor (GR) and the immunosuppressive treatment of step d) comprises a corticosteroid such as dexamethasone. As another embodiment, said target gene of step (b), specific for an immunosuppressive treatment, is a FKBP family gene member or a variant thereof and the immunosuppressive treatment of step (d) comprises FK506 also known as Tacrolimus or fujimycin. As another embodiment, said FKBP family gene member is FKBP12 or a variant thereof. As another embodiment, said gene of step (b), specific for an immunosuppressive treatment, is a cyclophilin family gene member or a variant thereof and the immunosuppressive treatment of step (d) comprises cyclosporine.

In a particular embodiment of the invention, the genetic modification step of the method relies on the inactivation of two genes selected from the group consisting of CD52 and GR, CD52 and TCR alpha, CDR52 and TCR beta, GR and TCR alpha, GR and TCR beta, TCR alpha and TCR beta. In another embodiment, the genetic modification step of the method relies on the inactivation of more than two genes. The genetic modification is preferably operated ex-vivo using at least two RNA guides targeting the different genes.

By inactivating a gene it is intended that the gene of interest is not expressed in a functional protein form.

Engineering Highly Active T Cells for Immunotherapy

In the scope of the present invention is also encompassed an isolated T cell obtained according to any one of the methods previously described. Said T-cell according to the present invention can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The T-cells according to the invention can be selected from the group consisting of inflammatory T-lymphocytes, cytotoxic T-lymphocytes, regulatory T-lymphocytes or helper T-lymphocytes. In another embodiment, said cell can be derived from the group consisting of CD4+T-lymphocytes and CD8+T-lymphocytes. Prior to expansion and genetic modification of the cells of the invention, a source of cells can be obtained from a subject through a variety of non-limiting methods. T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

Immune Check Points

It will be understood by those of ordinary skill in the art, that the term "immune checkpoints" means a group of molecules expressed by T cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1, SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7, SIGLEC9, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3 which directly inhibit immune cells. For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune checkpoint, in particular PD1 and/or CTLA-4 or any immune-checkpoint proteins referred to in Table 3.

In a preferred embodiment, at least two genes encoding immune checkpoint proteins are inactivated, selected from the group consisting of: CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3.

In a further preferred embodiment, the above immune checkpoint protein inactivation is combined with the previous proposed inactivation, in particular of TCR components.

In another preferred embodiment, said engineered T-cell according to the present invention comprises two inactivated genes selected from the group consisting of CD52 and GR, CD52 and TCR alpha, CDR52 and TCR beta, GR and TCR alpha, GR and TCR beta, TCR alpha and TCR beta, PD1 and TCR alpha, PD1 and TCR beta, CTLA-4 and TCR alpha, CTLA-4 and TCR beta, LAG3 and TCR alpha, LAG3 and TCR beta, Tim3 and TCR alpha, Tim3 and TCR beta, BTLA and TCR alpha, BTLA and TCR beta, BY55 and TCR alpha, BY55 and TCR beta, TIGIT and TCR alpha, TIGIT and TCR beta, B7H5 and TCR alpha, B7H5 and TCR beta, LAIR1 and TCR alpha, LAIR1 and TCR beta, SIGLEC10 and TCR alpha, SIGLEC10 and TCR beta, 2B4 and TCR alpha, 2B4 and TCR beta and/or expresses a CAR or a multi-chain CAR.

Engineered T-Cells Expressing Chimeric Antigen Receptors Against Malignant Cells Single-Chain CAR Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

TABLE 3

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The present invention further includes the possibility of expressing a chimeric antigen receptor as described in the literature in engineered T-cells as described herein.

CD19 is an attractive target for immunotherapy because the vast majority of B-acute lymphoblastic leukemia (B-ALL) uniformly express CD19, whereas expression is absent on non-hematopoietic cells, as well as myeloid, erythroid, and T cells, and bone marrow stem cells. Clinical trials targeting CD19 on B-cell malignancies are underway with encouraging anti-tumor responses. Most infuse T cells genetically modified to express a chimeric antigen receptor (CAR) with specificity derived from the scFv region of a CD19-specific mouse monoclonal antibody FMC63 (Nicholson, Lenton et al. 1997; Cooper, Topp et al. 2003; Cooper, Jena et al. 2012) (International application: WO2013/126712).

As an example of single-chain chimeric antigen receptor to be expressed in the genetically engineered T-cells according to the present invention is a single polypeptide that comprises at least one extracellular ligand binding domain, a transmembrane domain and at least one signal transducing domain, wherein said extracellular ligand binding domain comprises a scFV derived from the specific anti-CD19 monoclonal antibody 4G7. Once transduced into the T-cell, for instance by using retroviral or lentiviral transduction, this CAR contributes to the recognition of CD19 antigen present at the surface of malignant B-cells involved in lymphoma or leukemia.

Other examples of chimeric antigen receptor can also be introduced in the T-cells according to the present invention, such as CAR bearing antigen receptors directed against multiple myeloma or lymphoblastic leukemia antigen markers, such as TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708), and FCRL5 (UNIPROT Q68SN8).

As further examples, the antigen of the target can be from any cluster of differentiation molecules (e.g. CD16, CD64, CD78, CD96, CLL1, CD116, CD117, CD71, CD45, CD71, CD123 and CD138), a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers. Antigens are not necessarily surface marker antigens but can be also endogenous small antigens presented by HLA class I at the surface of the cells.

Multi-Subunit CAR

Chimeric antigen receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcεRI to allow normal juxtamembrane position of all relevant signaling domains. In this new architecture, the high affinity IgE binding domain of FcεRI alpha chain is replaced by an extracellular ligand-binding domain such as scFv to redirect T-cell specificity against cell targets and the N and/or C-termini tails of FcεRI beta chain are used to place costimulatory signals in normal juxtamembrane positions.

Accordingly, the CAR expressed by the engineered T-cell according to the invention can be a multi-chain chimeric antigen receptor (CAR) particularly adapted to the production and expansion of engineered T-cells of the present invention. Such multi-chain CARs comprise at least two of the following components:
a) one polypeptide comprising the transmembrembrane domain of FcεRI alpha chain and an extracellular ligand-binding domain,
b) one polypeptide comprising a part of N- and C-terminal cytoplasmic tail and the transmembrane domain of FcεRI beta chain and/or
c) at least two polypeptides comprising each a part of intracytoplasmic tail and the transmembrane domain of FcεRI gamma chain, whereby different polypeptides multimerize together spontaneously to form dimeric, trimeric or tetrameric CAR.

According to such architectures, ligands binding domains and signaling domains are born on separate polypeptides. The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently described by the applicant in PCT/US2013/058005.

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cambier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FcεRI beta and/or gamma chain fused to a signal-transducing domain and several part of FcεRI alpha chains fused to different extracellular ligand binding domains. In a more particular embodiment, said method comprises introducing into said cell at least one polynucleotide which encodes a part of FcεRI beta and/or gamma chain fused to a signal-transducing domain and several FcεRI alpha chains fused to different extracellular ligand binding domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies.

Bispecific or multi-specific CARs as described in WO 2014/4011988 also enter the scope of the present invention.

Activation and Expansion of T Cells

Whether prior to or after genetic modification of the T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with a surface having attached thereto an agent that stimulates a CD3 TCR complex associated signal and a ligand that stimulates a co-stimulatory molecule on the surface of the T cells.

In particular, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

The T-cells obtainable by the different methods described above are intended to be used as a medicament for treating, among others, cancer, infections or immune diseases in a patient in need thereof.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor.

By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product. Cells that can be used with the disclosed methods are described in the previous section.

Said treatments are primarily to treat patients diagnosed with cancer, viral infection, autoimmune disorders or Graft versus Host Disease (GvHD). Cancers are preferably leukemias and lymphomas, which have liquid tumors, but may also concern solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

The present T-cells, when armed with specific CARs directed against patient's own immune cells, allow the inhibition or regulation of said cells, which is a key step for treating auto-immune disease, such as rheumatoid polyarthritis, systemic lupus erythematosus, Sjogren's syndrome, scleroderma, fibromyalgia, myositis, ankylosing spondylitis, insulin dependent diabetes of type I, Hashimoto's thyroiditis, Addison's disease, Crohn's disease, Celiac's disease, amyotrophic lateral sclerosis (ALS) and multiple sclerosis (MS).

The treatment can take place in combination with one or more therapies selected from the group of antibodies therapy, chemotherapy, cytokines therapy, dendritic cell therapy, gene therapy, hormone therapy, laser light therapy and radiation therapy.

According to a preferred embodiment of the invention, said treatment are particularly suited for patients undergoing immunosuppressive or chemotherapy treatments. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

According to one embodiment, said T cells of the invention can undergo robust in vivo T cell expansion upon administration to a patient, and can persist in the body fluids for an extended amount of time, preferably for a week, more preferably for 2 weeks, even more preferably for at least one month. Although the T-cells according to the invention are expected to persist during these periods, their life span into the patient's body are intended not to exceed a year, preferably 6 months, more preferably 2 months, and even more preferably one month.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycopliencolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "polynucleotide successively comprising a first region of homology to sequences upstream of said double-stranded break, a sequence to be inserted in the genome of said cell and a second region of homology to sequences downstream of said double-stranded break" it is intended to mean a DNA construct or a matrix comprising a first and second portion that are homologous to regions 5' and 3' of a DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and this matrix, wherein the genomic sequence containing the DNA target is replaced by the third portion of the matrix and a variable part of the first and second portions of said matrix.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "delivery vector" or "delivery vectors" is intended any delivery vector which can be used in the present invention to put into cell contact (i.e. "contacting") or deliver inside cells or subcellular compartments (i.e. "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, or penetrating peptides. In these later cases, delivery vectors are molecule carriers.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non-limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1: General Method to Engineer Human Allogeneic Cells for Immunotherapy

Figure 4:
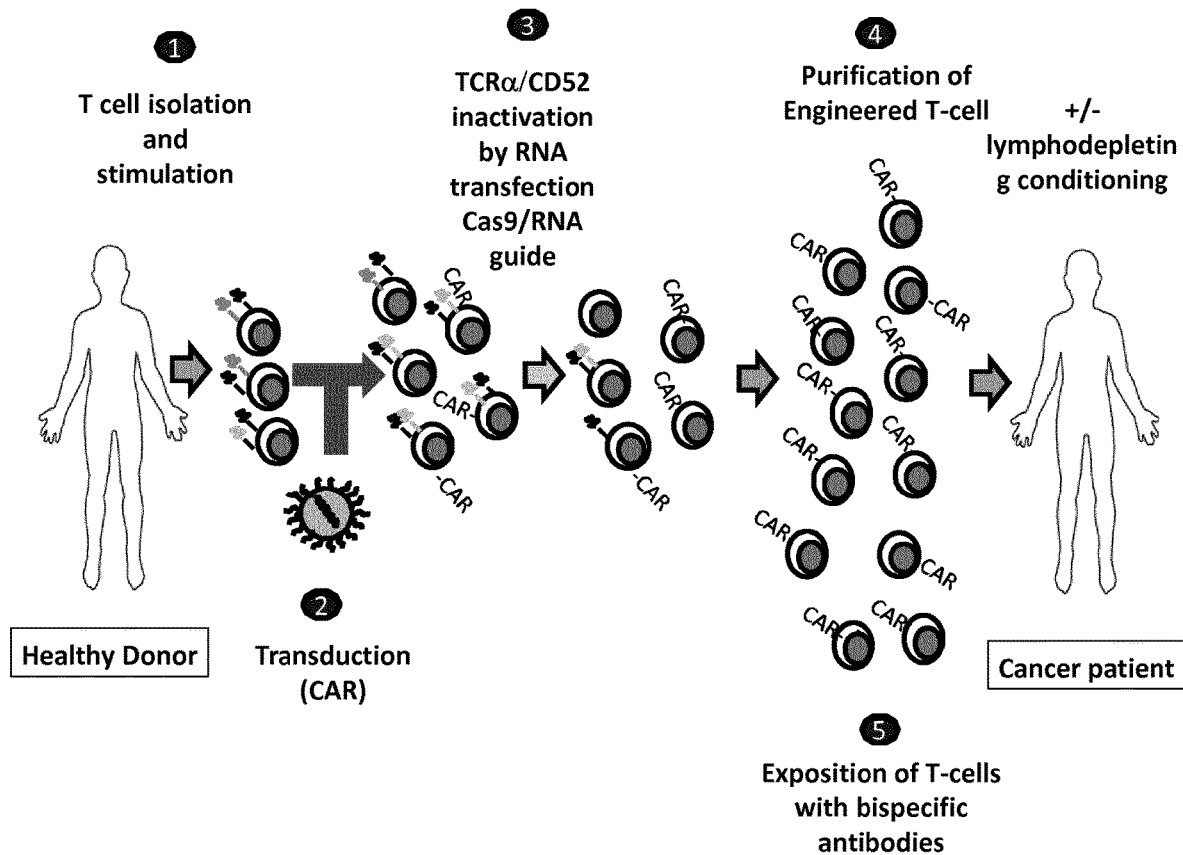
FIG. 4: Schematic representation of one example of the method of engineering human allogenic cells for immunotherapy.

For a better understanding of the invention, method to engineer human allogenic cells for immunotherapy is illustrated in FIG. 4. The method comprising a combination of one or several of the following steps:

1. Providing T-cells from a cell culture or from a blood sample from one individual patient or from blood bank and activating said T cells using anti-CD3/C28 activator beads. The beads provide both the primary and co-stimulatory signals that are required for activation and expansion of T cells.
2. Transducing said cells with multi-chain CARs allow redirecting T cells against antigens expressed at the surface of target cells from various malignancies including lymphomas and solid tumors, in particular against the antigen CD19. To improve the function of co-stimulatory domain, the inventors have designed a multi-chain CAR derived from FcεRI as previously described. Transduction can be realized before or after the gene inactivations using the RNA guided endonuclease.
3. Engineering non alloreactive and optionally resistant T cells:
   a) It is possible to Inactivate TCR alpha in said cells to eliminate the TCR from the surface of the cell and prevent recognition of host tissue as foreign by TCR of allogenic and thus to avoid GvHD.
   b) It is also possible to inactive one gene encoding target for an immunosuppressive agent or a chemotherapy drug to render said cells resistant to immunosuppressive or chemotherapy treatment treatment to prevent graft rejection without affecting transplanted T cells. In this example, target of immunosuppressive agents is CD52 and immunosuppressive agent is a humanized monoclonal anti-CD52 antibody.

As shown below by the inventors, the use of RNA guided endonuclease is particularly advantageous to achieve double gene inactivations in T-cells by merely introducing two distinct guide-RNA (gRNA), each targeting one gene, such as TCRalpha and CD52 genes. This can be done by electoporating T cells with mRNA encoding Cas9 and simultaneously transcription of DNA plasmids coding for the specific gRNA. Alternatively, the gRNA may be transcribed from DNA sequences stably integrated into the genome using retroviral vectors. It has been found by the inventors that transiently expressing Cas9 from mRNA resulted into high transformation rate and was less harmful to T-cells. Then, inactivated T cells are sorted using magnetic beads. For example, T cells still expressing the targeted gene (e.g. CD52) can be removed by fixation on a solid surface, and inactivated cells are not exposed of the stress of being passed through a column. This gentle method increases the concentration of properly engineered T-cells.
4. Expansion in vitro of engineered T-cells prior to administration to a patient or in vivo following administration to a patient through stimulation of CD3 complex. Before administration step, patients can be subjected to an immunosuppressive treatment such as CAMPATH1-H, a humanized monoclonal anti-CD52 antibody.
5. Optionally exposed said cells with bispecific antibodies ex vivo prior to administration to a patient or in vivo following administration to a patient to bring the engineered cells into proximity to a target antigen.

Example 2: Specific Inactivation of TCR and CD52 Genes in the T-Cells

1—CAS9 and gRNA Plasmids Construction

The sequence encoding the Cas9 from *S. pyogenes* was synthesized de novo (GeneCust) and flanked by 3×NLS and a HA tag at the C-terminus (pCLS22972 (SEQ ID NO. 53)). Sequences encoding the gRNA targeting the respective 20 bp sequences (5' to 3') in the TCRa gene (SEQ ID NO.54) and the CD52 gene (SEQ ID NO. 55) were cloned in pUC57 derived plasmid downstream an U6 promoter leading to respectively pCLS24029 (SEQ ID NO. 56) and pCLS24027 (SEQ ID NO. 57) plasmid vectors.

2—CAS9 mRNA Synthesis mRNA encoding CAS9 was produced and polyadenylated using the mMessage mMachine T7 Ultra kit (Life technologies) following the manufacturer's instructions. The RNA was subsequently purified with RNeasy columns (Qiagen), eluted in electroporation buffer, and quantified (Nanodrop ND-1000 spectrophotometer) by measuring absorbance at 260 nm. Quality of the RNA was verified on a denaturing formaldehyde/MOPS agarose gel.

3—Transfections

Figure 5:
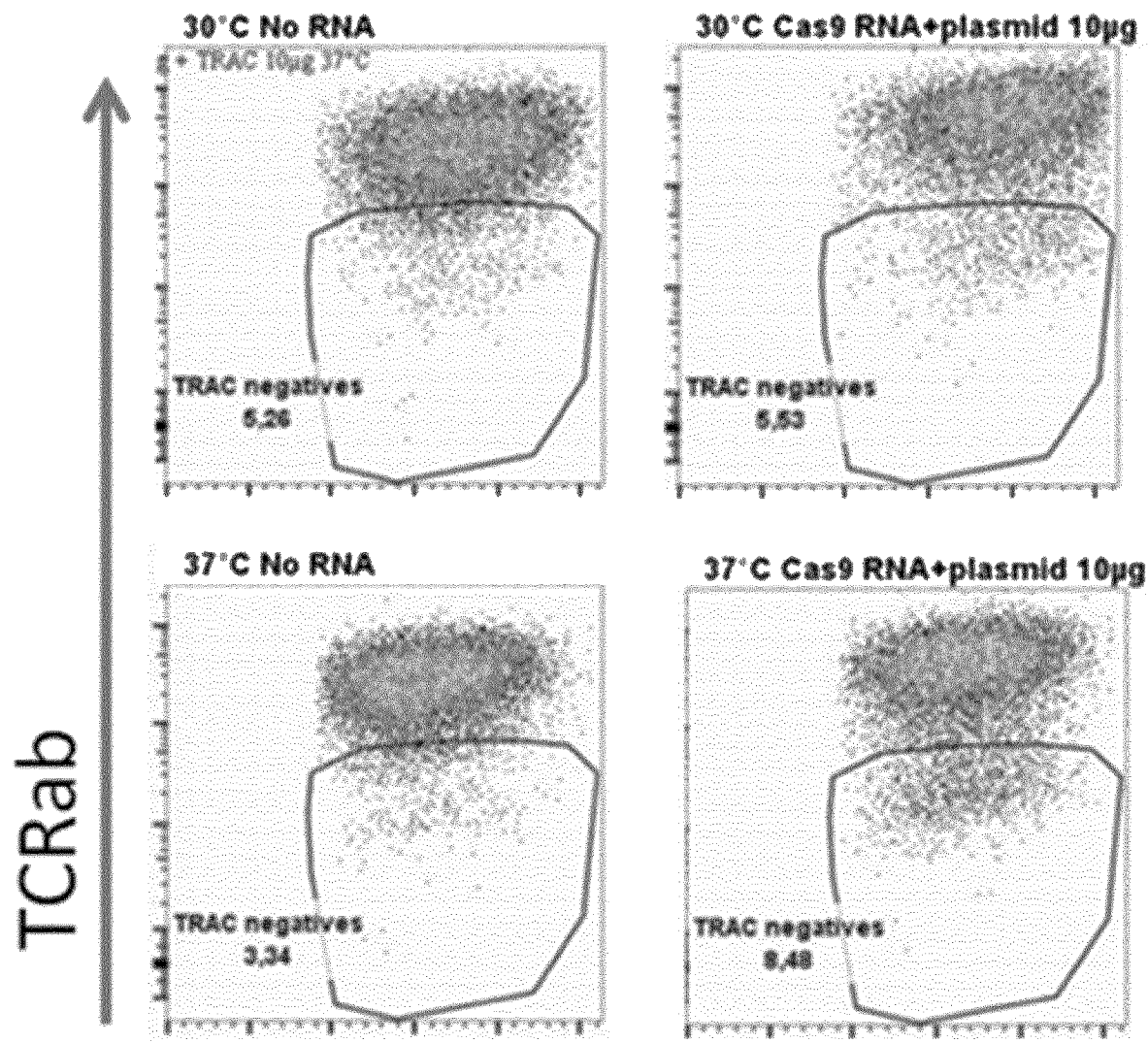
FIG. 5: Flow cytometry analysis of the activity of CRISPR system in T cells with respect to TCR gene (experimental results from example 2)—$5 \times 10^6$ T cells were transfected with 10 μg Cas9 mRNA+10 μg plasmid DNA expressing sgRNA specific for TRAC genes under the control of U6 promoter in the presence of a caspase inhibitor. Readout: 3 days post transfection, flow cytometry analysis using TCRαβ antibody. Controls: untransfected cells.
Figure 6:
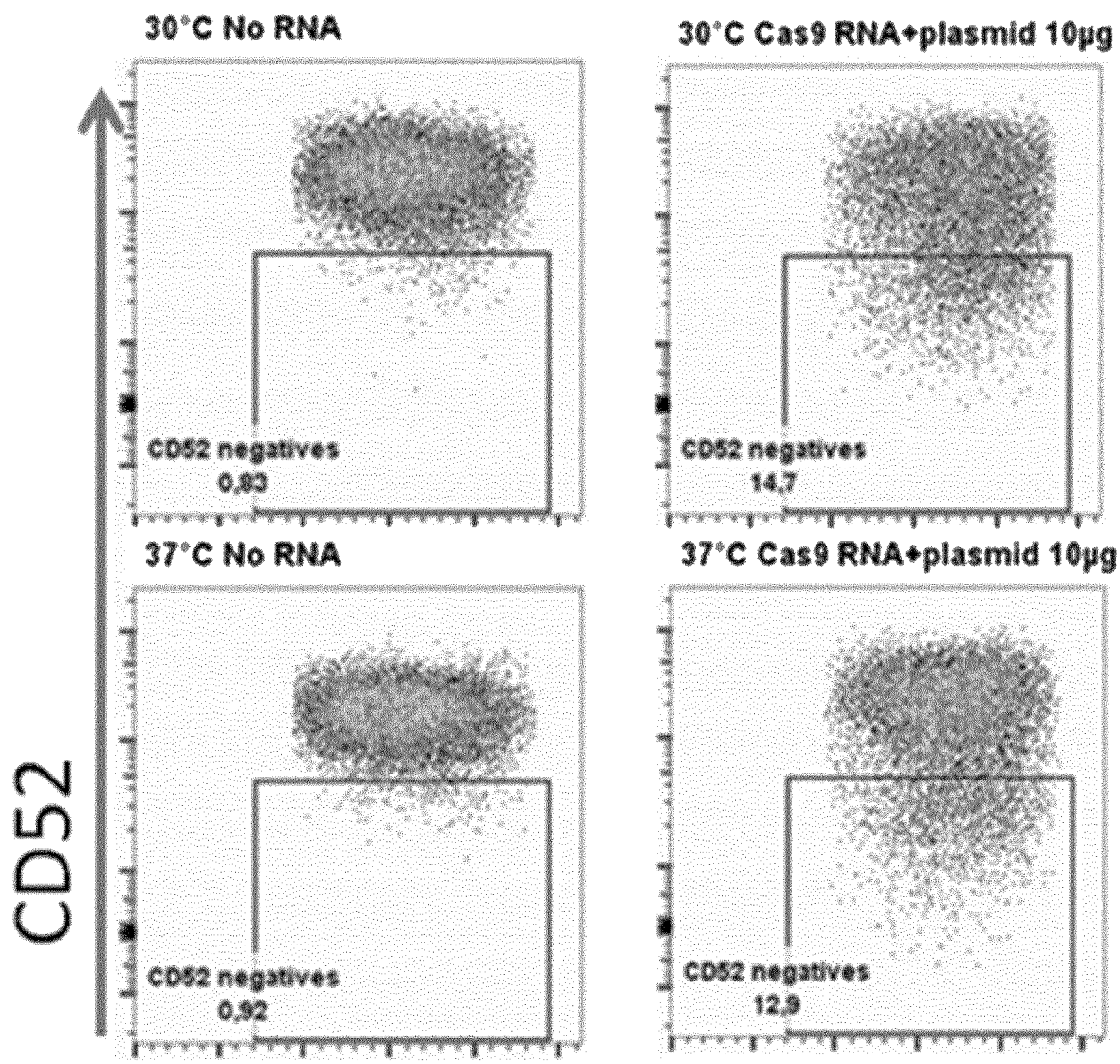
FIG. 6: Flow cytometry analysis of the activity of CRISPR system in T cells with respect to CD52 gene (experimental results from example 2)—$5 \times 10^6$ T cells were transfected with 10 μg Cas9 mRNA+10 μg plasmid DNA expressing sgRNA specific for CD52 genes under the control of U6 promoter in the presence of a caspase inhibitor. Readout: 3 days post transfection, flow cytometry analysis using CD52 antibody. Controls: untransfected cells.

T lymphocytes cells were transfected by electrotransfer of mRNA coding for the CAS9 and plasmids coding for gRNA using an AgilePulse MAX system (Harvard Apparatus) 4 days after activation (Dynabeads® Human T-Activator CD3/CD28, Life technologies). Briefly, T-cells were preactivated several days (3-5) pre-transfection with anti-CD3/CD28 coated beads and IL2. One day before electroporation, culture medium was changed and cells were seeded at $10^6$ cells/ml; 24h later, T-cells were washed in cytoporation medium T (Harvard Apparatus), activation beads were removed by decanting the T-cells suspension from a tube inserted in an EasySep magnet (StemCell technologies). T-cells were then pelleted, resuspended in cytoporation medium T at $25\times10^6$ cells/ml. $5\times10^6$ cells were mixed with 10 µg of the mRNA encoding the CAS9 and the plasmids encoding the gRNA targeting TCRa or into a 0.4 cm cuvette. The electroporation consisted of two 0.1 ms pulses at 1200 V followed by four 0.2 ms pulses at 130 V. Following electroporation, T-cells were diluted into culture medium and incubated at 37° C./5% $CO_2$ for 24 hours before another medium change. 3 days post electroporation, T-cells were stained with a fixable viability dye eFluor-780 and a PE or APC-conjugated goat anti mouse IgG F(ab')2 fragment specific to assess the cell surface expression of the TCRa or the CD52 respectively. Knock-out of either the TCRa or CD52 genes was analyzed (MACSQuant) by flow cytometry. The results are displayed in FIGS. 5 and 6, which show that TCR and CD52 genes have been respectively inactivated in a significant proportion of the analyzed cells.

Example 3: Functional Analysis of the Engineered T-Cells Electroporated with a Monocistronic mRNA Encoding for an Anti-CD19 Single Chain Chimeric Antigen Receptor (CAR)

To verify that genome engineering did not affect the ability of the engineered T-cells to present anti-tumor activity when provided with a chimeric antigen receptor (CAR CD19), The T-cells previously targeted using Cas9 and the specific guide RNA targeting TCRα, were further transfected with 10 µg of RNA encoding an anti-CD19 CAR. 24 hours later, T cells were incubated for 4 hours with CD19 expressing Daudi cells. The cell surface upregulation of CD107a, a marker of cytotoxic granule release by T lymphocytes (called degranulation) was measured by flow cytometry analysis (Betts, Brenchley et al. 2003).

$5\times10^6$ T cells preactivated several days (3-5) with anti-CD3/CD28 coated beads and IL2 were resuspended in cytoporation buffer T, and electroporated in 0.4 cm cuvettes without mRNA or with 10 µg of mRNA encoding a single chain CAR 24 hours post electroporation, cells were stained with a fixable viability dye eFluor-780 and a PE-conjugated goat anti mouse IgG F(ab')2 fragment specific to assess the cell surface expression of the CAR on the live cells. The data is shown in the FIG. 20. A indicates that the vast majority of the live T cells electroporated with the monocistronic mRNA described previously express the CAR at their surface. 24 hours post electroporation, T cells were cocultured with Daudi (CD19+) cells for 6 hours and analyzed by flow cytometry to detect the expression of the degranulation marker CD107a at their surface (Betts, Brenchley et al. 2003).

The results showed that TCRα-negative cells and TCRα-positive T-cells had the same ability to degranulate in response to PMA/ionomycin (positive control) or CD19+ Daudi cells. CD107 upregulation is dependent on the presence of a CD19+. These data suggest that genome engineering using Cas9 had no negative impact on the ability of T cells to mount a controlled anti-tumor response.

LIST OF REFERENCES CITED IN THE DESCRIPTION

Arimondo, P. B., C. J. Thomas, et al. (2006). "Exploring the cellular activity of camptothecin-triple-helix-forming oligonucleotide conjugates." *Mol Cell Biol* 26(1): 324-33.

Ashwell, J. D. and R. D. Klusner (1990). "Genetic and mutational analysis of the T-cell antigen receptor." *Annu Rev Immunol* 8: 139-67.

Bardenheuer, W., K. Lehmberg, et al. (2005). "Resistance to cytarabine and gemcitabine and in vitro selection of transduced cells after retroviral expression of cytidine deaminase in human hematopoietic progenitor cells." *Leukemia* 19(12): 2281-8.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boni, A., P. Muranski, et al. (2008). "Adoptive transfer of allogeneic tumor-specific T cells mediates effective regression of large tumors across major histocompatibility barriers." *Blood* 112(12): 4746-54.

Brahmer, J. R., C. G. Drake, et al. (2010). "Phase I study of single-agent anti-programmed death-1 (MDX-1106) in refractory solid tumors: safety, clinical activity, pharmacodynamics, and immunologic correlates." *J Clin Oncol* 28(19): 3167-75.

Cambier, J. C. (1995). "Antigen and Fc receptor signaling. The awesome power of the immunoreceptor tyrosine-based activation motif (ITAM)." *J Immunol* 155(7): 3281-5.

Carrasco, Y. R. et al. (2001). "An endoplasmic reticulum retention function for the cytoplasmic tail of the human pre-T cell receptor (TCR) alpha chain: potential role in the regulation of cell surface pre-TCR expression levels." *J Exp Med* 193(9):1045-58.

Cho, S. W. et al. (2013). "Targeted genome engineering in human cells with the Cas9 RNA-guided endonuclease". *Nature Biotechnology* 31: 230-232

Cong, L., F. A. Ran, et al. (2013). "Multiplex genome engineering using CRISPR/Cas systems." *Science* 339 (6121): 819-23

Cooper, L. J. N. (2003). "T-cell clones can be rendered specific for CD19: toward the selective augmentation of the graft-versus-B-lineage leukemia effect". *Blood* 101 (4):1637-1644.

Coutinho, A. E. and K. E. Chapman (2011). "The anti-inflammatory and immunosuppressive effects of glucocorticoids, recent developments and mechanistic insights." *Mol Cell Endocrinol* 335(1): 2-13.

Critchlow, S. E. and S. P. Jackson (1998). "DNA end-joining: from yeast to man." *Trends Biochem* Sci 23(10): 394-8.

Dalgaard, J. Z., A. J. Klar, et al. (1997). "Statistical modeling and analysis of the LAGLIDADG (SEQ ID NO: 58) family of site-specific endonucleases and identification of an intein that encodes a site-specific endonuclease of the HNH family." *Nucleic Acids Res* 25(22): 4626-38.

Deltcheva, E., K. Chylinski, et al. (2011). "CRISPR RNA maturation by trans-encoded small RNA and host factor RNase III." *Nature* 471(7340): 602-7.

Deveau, H., R. Barrangou, et al. (2008). "Phage response to CRISPR-encoded resistance in *Streptococcus thermophilus.*" *J Bacteriol* 190(4): 1390-400

Eisenschmidt, K., T. Lanio, et al. (2005). "Developing a programmed restriction endonuclease for highly specific DNA cleavage." *Nucleic Acids Res* 33(22): 7039-47.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Geissler, R., H. Scholze, et al. (2011). "Transcriptional activators of human genes with programmable DNA-specificity." *PLoS One* 6(5): e19509.

Gorbalenya, A. E. (1994). "Self-splicing group I and group II introns encode homologous (putative) DNA endonucleases of a new family." *Protein Sci* 3(7): 1117-20.

Haft, D. H., J. Selengut, et al. (2005). "A guild of 45 CRISPR-associated (Cas) protein families and multiple CRISPR/Cas subtypes exist in prokaryotic genomes." *PLoS Comput Biol* 1(6): e60

Howard, F. D., H. R. Rodewald, et al. (1990). "CD3 zeta subunit can substitute for the gamma subunit of Fc epsilon receptor type I in assembly and functional expression of the high-affinity IgE receptor: evidence for interceptor complementation." *Proc Natl Acad Sci USA* 87(18): 7015-9.

Huang, P., A. Xiao, et al. (2011). "Heritable gene targeting in zebrafish using customized TALENs." *Nat Biotechnol* 29(8): 699-700.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Jonnalagadda, M., C. E. Brown, et al. (2013). "Engineering human T cells for resistance to methotrexate and mycophenolate mofetil as an in vivo cell selection strategy." *PLoS One* 8(6): e65519.

Kleanthous, C., U. C. Kuhlmann, et al. (1999). "Structural and mechanistic basis of immunity toward endonuclease colicins." *Nat Struct Biol* 6(3): 243-52.

Kushman, M. E., S. L. Kabler, et al. (2007). "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1." *Carcinogenesis* 28(1): 207-14.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mak, A. N., P. Bradley, et al. (2012). "The crystal structure of TAL effector PthXo1 bound to its DNA target." *Science* 335(6069): 716-9.

Makarova, K. S., N. V. Grishin, et al. (2006). "A putative RNA-interference-based immune system in prokaryotes: computational analysis of the predicted enzymatic machinery, functional analogies with eukaryotic RNAi, and hypothetical mechanisms of action." *Biol Direct* 1: 7

Mali, P., L. Yang, et al. (2013). "RNA-guided human genome engineering via Cas9." *Science* 339(6121): 823-6.

Metzger, H., G. Alcaraz, et al. (1986). "The receptor with high affinity for immunoglobulin E." *Annu Rev Immunol* 4: 419-70.

Mojica, F. J., C. Diez-Villasenor, et al. (2009). "Short motif sequences determine the targets of the prokaryotic CRISPR defence system." *Microbiology* 155(Pt 3): 733-40

Nicholson, I. C. (1997) "Construction and characterisation of a functional CD19 specific single chain Fv fragment for immunotherapy of B lineage leukaemia and lymphoma". *Molecular Immunology* 34(16):1157-1165.

Nivens, M. C., T. Felder, et al. (2004). "Engineered resistance to camptothecin and antifolates by retroviral coexpression of tyrosyl DNA phosphodiesterase-I and thymidylate synthase." *Cancer Chemother Pharmacol* 53(2): 107-15

Pang, S. S., R. Berry, et al. (2010). "The structural basis for autonomous dimerization of the pre-T-cell antigen receptor." *Nature* 467(7317): 844-8.

Pardoll, D. and C. Drake (2012). "Immunotherapy earns its spot in the ranks of cancer therapy." *J Exp Med* 209(2): 201-9.

Pardoll, D. M. (2012). "The blockade of immune checkpoints in cancer immunotherapy." *Nat Rev Cancer* 12(4): 252-64.

Park, T. S., S. A. Rosenberg, et al. (2011). "Treating cancer with genetically engineered T cells." *Trends Biotechnol* 29(11): 550-7.

Robert, C. and C. Mateus (2011). "[Anti-CTLA-4 monoclonal antibody: a major step in the treatment of metastatic melanoma]." *Med Sci (Paris)* 27(10): 850-8.

Saint-Ruf, C., O. Lechner, et al. (1998). "Genomic structure of the human pre-T cell receptor alpha chain and expression of two mRNA isoforms." *Eur J Immunol* 28(11): 3824-31.

Sangiolo, D., M. Lesnikova, et al. (2007). "Lentiviral vector conferring resistance to mycophenolate mofetil and sensitivity to ganciclovir for in vivo T-cell selection." *Gene Ther* 14(21): 1549-54.

Sapranauskas, R., G. Gasiunas, et al. (2011). "The *Streptococcus thermophilus* CRISPR/Cas system provides immunity in *Escherichia coli*." *Nucleic Acids Res* 39(21): 9275-82.

Schutz, K., J. R. Hesselberth, et al. (2010). "Capture and sequence analysis of RNAs with terminal 2',3'-cyclic phosphates." *RNA* 16(3): 621-31.

Shub, D. A., H. Goodrich-Blair, et al. (1994). "Amino acid sequence motif of group I intron endonucleases is conserved in open reading frames of group II introns." *Trends Biochem Sci* 19(10): 402-4.

Schweitzer, B. I., A. P. Dicker, et al. (1990). "Dihydrofolate reductase as a therapeutic target." *Faseb J* 4(8): 2441-52.

Sugimoto, Y., S. Tsukahara, et al. (2003). "Drug-selected co-expression of P-glycoprotein and gp91 in vivo from an MDR1-bicistronic retrovirus vector Ha-MDR-IRES-gp91." *J Gene Med* 5(5): 366-76.

Takebe, N., S. C. Zhao, et al. (2001). "Generation of dual resistance to 4-hydroperoxycyclophosphamide and methotrexate by retroviral transfer of the human aldehyde dehydrogenase class 1 gene and a mutated dihydrofolate reductase gene." *Mol Ther* 3(1): 88-96.

Van der Ploeg, J. R. (2009). "Analysis of CRISPR in *Streptococcus mutans* suggests frequent occurrence of acquired immunity against infection by M102-like bacteriophages." *Microbiology* 155(Pt 6): 1966-76 von Boehmer, H. (2005). "Unique features of the pre-T-cell receptor alpha-chain: not just a surrogate." *Nat Rev Immunol* 5(7): 571-7.

Waldmann, H. and G. Hale (2005). "CAMPATH: from concept to clinic." *Philos Trans R Soc Lond B Biol Sci* 360(1461): 1707-11.

Yam, P., M. Jensen, et al. (2006). "Ex vivo selection and expansion of cells based on expression of a mutated inosine monophosphate dehydrogenase 2 after HIV vector transduction: effects on lymphocytes, monocytes, and CD34+ stem cells." *Mol Ther* 14(2): 236-44

Zielske, S. P., J. S. Reese, et al. (2003). "In vivo selection of MGMT(P140K) lentivirus-transduced human NOD/SCID repopulating cells without pretransplant irradiation conditioning." *J Clin Invest* 112(10): 1561-70

The invention claimed is:

1. A method of preparing and administering T-cells for immunotherapy comprising the steps of:
   (a) providing primary human T-cells from a donor,
   (b) genetically modifying the primary human T-cells to eliminate expression of the T-cell receptor (TCR), comprising expressing in the cells
      (i) a Cas9 endonuclease fused to a nuclear localization signal (NLS), and
      (ii) a guide RNA that directs said endonuclease to at least one targeted locus encoding the TCR in the T-cell genome,
   (c) expanding the genetically modified T-cells, and
   (d) administering at least $10^4$ of the expanded genetically modified T-cells to a patient.

2. The method of claim 1, comprising administering at least $10^5$ of the expanded genetically modified T-cells to a patient.

3. The method of claim 1, comprising administering at least $10^6$ of the expanded genetically modified T-cells to a patient.

4. The method of claim 1, comprising administering at least $10^7$ of the expanded genetically modified T-cells to a patient.

5. The method of claim 1, comprising administering at least $10^8$ of the expanded genetically modified T-cells to a patient.

6. The method of claim 1, comprising administering at least $10^9$ of the expanded genetically modified T-cells to a patient.

7. The method of claim 1, wherein expression of the T-cell receptor is eliminated by cleavage within the TCRα gene.

8. The method of claim 1, wherein expression of the T-cell receptor is eliminated by cleavage within the TCRβ gene.

9. The method of claim 1, further comprising introducing into the genetically modified T-cells a chimeric antigen receptor (CAR).

10. The method of claim 9, wherein the CAR is an anti-CD19 CAR.

11. The method of claim 2, further comprising introducing into the genetically modified T-cells a CAR.

12. The method of claim 11, wherein the CAR is an anti-CD19 CAR.

13. The method of claim 3, further comprising introducing into the genetically modified T-cells a CAR.

14. The method of claim 13, wherein the CAR is an anti-CD19 CAR.

15. The method of claim 4, further comprising introducing into the genetically modified T-cells a CAR.

16. The method of claim 15, wherein the CAR is an anti-CD19 CAR.

17. The method of claim 5, further comprising introducing into the genetically modified T-cells a CAR.

18. The method of claim 17, wherein the CAR is an anti-CD19 CAR.

19. The method of claim 6, further comprising introducing into the genetically modified T-cells a CAR.

20. The method of claim 19, wherein the CAR is an anti-CD19 CAR.

* * * * *

SEQUENCE LISTING

```
<160> NUMBER OF SEQ ID NOS: 66

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      RuvC motif peptide
<220> FEATURE:
<221> NAME/KEY: MOD_RES
<222> LOCATION: (2)..(2)
<223> OTHER INFORMATION: Ile or Leu
<220> FEATURE:
<221> NAME/KEY: MOD_RES
<222> LOCATION: (4)..(5)
<223> OTHER INFORMATION: Any naturally occurring amino acid
<220> FEATURE:
<221> NAME/KEY: MOD_RES
<222> LOCATION: (7)..(7)
<223> OTHER INFORMATION: Any naturally occurring amino acid

<400> SEQUENCE: 1

Asp Xaa Gly Xaa Xaa Ser Xaa Gly Trp Ala
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      HNH motif peptide
<220> FEATURE:
<221> NAME/KEY: MOD_RES
<222> LOCATION: (2)..(3)
<223> OTHER INFORMATION: Any naturally occurring amino acid
<220> FEATURE:
<221> NAME/KEY: MOD_RES
```

```
<222> LOCATION: (6)..(7)
<223> OTHER INFORMATION: Any naturally occurring amino acid
<220> FEATURE:
<221> NAME/KEY: MOD_RES
<222> LOCATION: (9)..(9)
<223> OTHER INFORMATION: Any naturally occurring amino acid
<220> FEATURE:
<221> NAME/KEY: MOD_RES
<222> LOCATION: (11)..(13)
<223> OTHER INFORMATION: Any naturally occurring amino acid
<220> FEATURE:
<221> NAME/KEY: MOD_RES
<222> LOCATION: (15)..(15)
<223> OTHER INFORMATION: Any naturally occurring amino acid

<400> SEQUENCE: 2

Tyr Xaa Xaa Asp His Xaa Xaa Pro Xaa Ser Xaa Xaa Xaa Asp Xaa Ser
1               5                   10                  15

<210> SEQ ID NO 3
<211> LENGTH: 1368
<212> TYPE: PRT
<213> ORGANISM: Streptococcus pyogenes
<220> FEATURE:
<223> OTHER INFORMATION: Serotype M1, Cas9

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
```

-continued

```
                260             265             270
Asp Asp Leu Asp Asn Leu Leu Ala Gln Ile Gly Asp Gln Tyr Ala Asp
            275             280             285

Leu Phe Leu Ala Ala Lys Asn Leu Ser Asp Ala Ile Leu Leu Ser Asp
            290             295             300

Ile Leu Arg Val Asn Thr Glu Ile Thr Lys Ala Pro Leu Ser Ala Ser
305             310             315             320

Met Ile Lys Arg Tyr Asp Glu His His Gln Asp Leu Thr Leu Leu Lys
            325             330             335

Ala Leu Val Arg Gln Gln Leu Pro Glu Lys Tyr Lys Glu Ile Phe Phe
            340             345             350

Asp Gln Ser Lys Asn Gly Tyr Ala Gly Tyr Ile Asp Gly Gly Ala Ser
            355             360             365

Gln Glu Glu Phe Tyr Lys Phe Ile Lys Pro Ile Leu Glu Lys Met Asp
            370             375             380

Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430

Leu Lys Asp Asn Arg Glu Lys Ile Glu Lys Ile Leu Thr Phe Arg Ile
            435             440             445

Pro Tyr Tyr Val Gly Pro Leu Ala Arg Gly Asn Ser Arg Phe Ala Trp
            450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
            530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
            610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
            675             680             685
```

-continued

```
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
```

```
Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 4
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: RuvC domain of S. pyogenes Cas9

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60
```

```
Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly
                165

<210> SEQ ID NO 5
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: large version of HNH domain of S. pyogenes Cas9

<400> SEQUENCE: 5

Pro Val Glu Asn Thr Gln Leu Gln Asn Glu Lys Leu Tyr Leu Tyr Tyr
 1               5                  10                  15

Leu Gln Asn Gly Arg Asp Met Tyr Val Asp Gln Glu Leu Asp Ile Asn
             20                  25                  30

Arg Leu Ser Asp Tyr Asp Val Asp His Ile Val Pro Gln Ser Phe Leu
         35                  40                  45

Lys Asp Asp Ser Ile Asp Asn Lys Val Leu Thr Arg Ser Asp Lys Asn
 50                  55                  60

Arg Gly Lys Ser Asp Asn Val Pro Ser Glu Glu Val Val Lys Lys Met
 65                  70                  75                  80

Lys Asn Tyr Trp Arg Gln Leu Leu Asn Ala Lys Leu Ile Thr Gln Arg
                 85                  90                  95

Lys Phe Asp Asn Leu Thr Lys Ala Glu Arg Gly Gly Leu Ser Glu Leu
            100                 105                 110

Asp Lys Ala Gly Phe Ile Lys Arg Gln Leu Val Glu Thr Arg Gln Ile
        115                 120                 125

Thr Lys His Val Ala Gln Ile Leu Asp Ser Arg Met Asn Thr Lys Tyr
    130                 135                 140

Asp Glu Asn Asp Lys Leu Ile Arg Glu Val Lys Val Ile Thr Leu Lys
145                 150                 155                 160

Ser Lys Leu Val Ser Asp Phe Arg Lys Asp Phe Gln Phe Tyr Lys Val
                165                 170                 175

Arg Glu Ile Asn Asn Tyr His His Ala His Asp Ala Tyr Leu Asn Ala
            180                 185                 190

Val Val Gly Thr Ala Leu Ile Lys Lys Tyr Pro Lys Leu Glu Ser Glu
        195                 200                 205

Phe Val Tyr Gly Asp Tyr Lys Val Tyr Asp Val Arg Lys Met Ile Ala
    210                 215                 220

Lys Ser Glu Gln Glu Ile Gly Lys Ala Thr Ala Lys Tyr Phe Phe Tyr
225                 230                 235                 240
```

Ser Asn Ile Met Asn Phe Phe Lys Thr Glu Ile Thr Leu Ala Asn Gly
            245                 250                 255

```
<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 6
gagaatcaaa atcggtgaat agg                                               23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 7
ttcaaaacct gtcagtgatt ggg                                               23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 8
tgtgctagac atgaggtcta tgg                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 9
cgtcatgagc agattaaacc cgg                                               23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 10
tcagggttct ggatatctgt ggg                                               23
```

```
<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 11
gtcagggttc tggatatctg tgg                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 12
ttcggaaccc aatcactgac agg                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 13
taaacccggc cactttcagg agg                                              23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 14
aaagtcagat tgttgctcc agg                                               23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 15
aacaaatgtg tcacaaagta agg                                              23

<210> SEQ ID NO 16
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 16
tggatttaga gtctctcagc tgg                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 17
taggcagaca gacttgtcac tgg                                              23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 18
agctggtaca cggcagggtc agg                                              23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 19
gctggtacac ggcagggtca ggg                                              23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 20
tctctcagct ggtacacggc agg                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Cas9 target TCR gene

<400> SEQUENCE: 21
tttcaaaacc tgtcagtgat tgg                                                23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 22
gattaaaccc ggccactttc agg                                                23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 23
ctcgaccagc ttgacatcac agg                                                23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 24
agagtctctc agctggtaca cgg                                                23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 25
ctctcagctg gtacacggca ggg                                                23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 26
aagttcctgt gatgtcaagc tgg                                            23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 27
atcctcctcc tgaaagtggc cgg                                            23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 28
tgctcatgac gctgcggctg tgg                                            23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 29
acaaaactgt gctagacatg agg                                            23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 30
atttgtttga gaatcaaaat cgg                                            23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 31
catcacagga actttctaaa agg                                            23

<210> SEQ ID NO 32

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 32
gtcgagaaaa gctttgaaac agg                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 33
ccactttcag gaggaggatt cgg                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 34
ctgacaggtt ttgaaagttt agg                                              23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 35
agctttgaaa caggtaagac agg                                              23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 36
tggaataatg ctgttgttga agg                                              23

<210> SEQ ID NO 37
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 37
agagcaacag tgctgtggcc tgg                                           23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 38
ctgtggtcca gctgaggtga ggg                                           23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 39
ctgcggctgt ggtccagctg agg                                           23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 40
tgtggtccag ctgaggtgag ggg                                           23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 41
cttcttcccc agcccaggta agg                                           23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene
```

```
<400> SEQUENCE: 42
acacggcagg gtcagggttc tgg                                            23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 43
cttcaagagc aacagtgctg tgg                                            23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 44
ctggggaaga aggtgtcttc tgg                                            23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 45
tcctcctcct gaaagtggcc ggg                                            23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 46
ttaatctgct catgacgctg cgg                                            23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 47
acccggccac tttcaggagg agg                                            23
```

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 48
ttcttcccca gcccaggtaa ggg                                            23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 49
cttacctggg ctggggaaga agg                                            23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 50
gacaccttct tccccagccc agg                                            23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 51
gctgtggtcc agctgaggtg agg                                            23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Cas9 target TCR gene

<400> SEQUENCE: 52
ccgaatcctc ctcctgaaag tgg                                            23

<210> SEQ ID NO 53
<211> LENGTH: 1410

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cas9 encoded by pCLS22972

<400> SEQUENCE: 53

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

```
                785                 790                 795                 800
Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                    820                 825                 830

Leu Ser Asp Tyr Asp Val Asp His Ile Val Pro Gln Ser Phe Leu Lys
                    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                    900                 905                 910

Lys Ala Gly Phe Ile Lys Arg Gln Leu Val Glu Thr Arg Gln Ile Thr
                    915                 920                 925

Lys His Val Ala Gln Ile Leu Asp Ser Arg Met Asn Thr Lys Tyr Asp
                    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                    965                 970                 975

Glu Ile Asn Asn Tyr His His Ala His Asp Ala Tyr Leu Asn Ala Val
                    980                 985                 990

Val Gly Thr Ala Leu Ile Lys Lys Tyr Pro Lys Leu Glu Ser Glu Phe
                    995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Ala Pro Lys Lys Lys Arg Lys Val Glu Ser Pro Lys Lys Lys
    1370                1375                1380

Arg Lys Val Glu Ser Pro Lys Lys Lys Arg Lys Val Glu Gly Asn
    1385                1390                1395

Ser Tyr Pro Tyr Asp Val Pro Asp Tyr Ala Ala Asp
    1400                1405                1410

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target TCRa

<400> SEQUENCE: 54
gtcagggttc tggatatctg                                                 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target CD52

<400> SEQUENCE: 55
ggaggctgat ggtgagtagg                                                 20

<210> SEQ ID NO 56
<211> LENGTH: 496
<212> TYPE: DNA
<213> ORGANISM: Artificial Sequence
<220> FEATURE:
```

<223> OTHER INFORMATION: Description of Artificial Sequence: Synthetic
polynucleotide
<220> FEATURE:
<223> OTHER INFORMATION: gRNA TCRa pCLS24029

<400> SEQUENCE: 56

```
cgcgcggccg cgcgtggccg gacgggccgg tacctgtaca aaaaagcagg ctttaaagga    60
accaattcag tcgactggat ccggtaccaa ggtcgggcag gaagagggcc tatttcccat   120
gattccttca tatttgcata tacgatacaa ggctgttaga gagataatta gaattaattt   180
gactgtaaac acaaagatat tagtacaaaa tacgtgacgt agaaagtaat aatttcttgg   240
gtagtttgca gttttaaaat tatgttttaa aatggactat catatgctta ccgtaacttg   300
aaagtatttc gatttcttgg ctttatatat cttgtggaaa ggacgaaaca ccgtcagggt   360
tctggatatc tggttttaga gctagaaata gcaagttaaa ataaggctag tccgttatca   420
acttgaaaaa gtggcaccga gtcggtgctt ttttttctaga cccagcaggt ggccactggg   480
gcccgcgaat cgcgt                                                     496
```

<210> SEQ ID NO 57
<211> LENGTH: 496
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: gRNA CD52 pCLS24027

<400> SEQUENCE: 57

```
cgcgcggccg cgcgtggccg gacgggccgg tacctgtaca aaaaagcagg ctttaaagga    60
accaattcag tcgactggat ccggtaccaa ggtcgggcag gaagagggcc tatttcccat   120
gattccttca tatttgcata tacgatacaa ggctgttaga gagataatta gaattaattt   180
gactgtaaac acaaagatat tagtacaaaa tacgtgacgt agaaagtaat aatttcttgg   240
gtagtttgca gttttaaaat tatgttttaa aatggactat catatgctta ccgtaacttg   300
aaagtatttc gatttcttgg ctttatatat cttgtggaaa ggacgaaaca ccggaggctg   360
atggtgagta gggttttaga gctagaaata gcaagttaaa ataaggctag tccgttatca   420
acttgaaaaa gtggcaccga gtcggtgctt ttttttctaga cccagcaggt ggccactggg   480
gcccgcgaat cgcgt                                                     496
```

<210> SEQ ID NO 58
<211> LENGTH: 9
<212> TYPE: PRT
<213> ORGANISM: Unknown
<220> FEATURE:
<223> OTHER INFORMATION: Description of Unknown: "LAGLIDADG" family
peptide motif

<400> SEQUENCE: 58

Leu Ala Gly Leu Ile Asp Ala Asp Gly
1               5

<210> SEQ ID NO 59
<211> LENGTH: 7
<212> TYPE: PRT
<213> ORGANISM: Simian virus 40

<400> SEQUENCE: 59

Pro Lys Lys Lys Arg Lys Val

```
1               5

<210> SEQ ID NO 60
<211> LENGTH: 16
<212> TYPE: PRT
<213> ORGANISM: Unknown
<220> FEATURE:
<223> OTHER INFORMATION: Description of Unknown: Nucleoplasmin
      peptide

<400> SEQUENCE: 60

Lys Arg Pro Ala Ala Thr Lys Lys Ala Gly Gln Ala Lys Lys Lys Lys
1               5                   10                  15

<210> SEQ ID NO 61
<211> LENGTH: 7
<212> TYPE: PRT
<213> ORGANISM: Unknown
<220> FEATURE:
<223> OTHER INFORMATION: Description of Unknown: p54 peptide

<400> SEQUENCE: 61

Arg Ile Arg Lys Lys Leu Arg
1               5

<210> SEQ ID NO 62
<211> LENGTH: 5
<212> TYPE: PRT
<213> ORGANISM: Unknown
<220> FEATURE:
<223> OTHER INFORMATION: Description of Unknown: SOX9 peptide

<400> SEQUENCE: 62

Pro Arg Arg Arg Lys
1               5

<210> SEQ ID NO 63
<211> LENGTH: 9
<212> TYPE: PRT
<213> ORGANISM: Unknown
<220> FEATURE:
<223> OTHER INFORMATION: Description of Unknown: NS5A
      peptide

<400> SEQUENCE: 63

Pro Pro Arg Lys Lys Arg Thr Val Val
1               5

<210> SEQ ID NO 64
<211> LENGTH: 16
<212> TYPE: PRT
<213> ORGANISM: Unknown
<220> FEATURE:
<223> OTHER INFORMATION: Description of Unknown: Cell-penetrating
      peptide peptide

<400> SEQUENCE: 64

Arg Gln Ile Arg Ile Trp Phe Gln Asn Arg Arg Met Arg Trp Arg Arg
1               5                   10                  15

<210> SEQ ID NO 65
<211> LENGTH: 17
<212> TYPE: PRT
<213> ORGANISM: Unknown
<220> FEATURE:
<223> OTHER INFORMATION: Description of Unknown: Cell-penetrating
      peptide peptide
```

```
<400> SEQUENCE: 65

Arg Gln Ile Arg Ile Trp Phe Gln Asn Arg Arg Met Arg Trp Arg Arg
1               5                   10                  15
Cys

<210> SEQ ID NO 66
<211> LENGTH: 17
<212> TYPE: PRT
<213> ORGANISM: Unknown
<220> FEATURE:
<223> OTHER INFORMATION: Description of Unknown: Cell-penetrating
      peptide peptide

<400> SEQUENCE: 66

Arg Gln Ile Lys Ile Trp Phe Gln Asn Arg Arg Met Lys Trp Lys Lys
1               5                   10                  15
Cys
```